United States Patent [19]
Mikoshiba et al.

[11] Patent Number: 5,227,359
[45] Date of Patent: Jul. 13, 1993

[54] HEAT TRANSFER DYE PROVIDING MATERIAL

[75] Inventors: Hisashi Mikoshiba; Mitsugu Tanaka; Seiiti Kubodera, all of Kanagawa, Japan

[73] Assignee: Fuji Photo Film Co., Ltd., Kanagawa, Japan

[21] Appl. No.: 740,248

[22] Filed: Aug. 5, 1991

[30] Foreign Application Priority Data

Aug. 3, 1990 [JP] Japan .................. 2-205223

[51] Int. Cl.⁵ .................. B41M 5/035; B41M 5/38
[52] U.S. Cl. .................. 503/227; 428/195; 428/913; 428/914
[58] Field of Search .................. 8/471; 428/195, 913, 428/914; 503/227

[56] References Cited

U.S. PATENT DOCUMENTS 5,034,371 7/1991 Tanaka et al. .................. 503/227

FOREIGN PATENT DOCUMENTS 0279467 8/1988 European Pat. Off. ............ 503/227

Primary Examiner—B. Hamilton Hess
Attorney, Agent, or Firm—Sughrue, Mion, Zinn, Macpeak & Seas

[57] ABSTRACT

Disclosed is a heat transfer dye providing material having on a support a dye providing layer containing a heat migrating dye, wherein the dye providing layer contains a heat migrating dye represented by following formula (I):

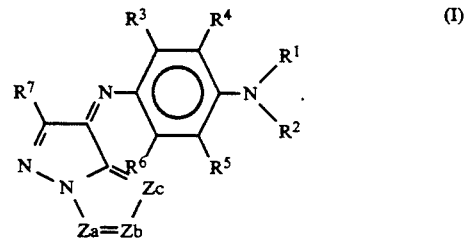

13 Claims, 1 Drawing Sheet

HEAT TRANSFER DYE PROVIDING MATERIAL

FIELD OF THE INVENTION

The present invention relates to a heat transfer dye providing material containing heat migrating dye(s).

BACKGROUND OF THE INVENTION

Heat transfer processes, electrophotographic processes, ink jet processes, etc., have been vigorously investigated as a technique for forming color hard copy. A heat transfer process has many advantages as compared to other processes since in a heat transfer process, the apparatus can be easily maintained and operated. The apparatus and the supplies therefor are inexpensive.

Such systems include a system of heating a heat transfer material composed of a base film having formed thereon a heat melting ink layer, by a thermal head to melt the ink and to record on a heat transfer image-receiving layer. Also known is a system of heating a heat transfer dye providing material composed of a base film having formed thereon a dye-providing layer containing a heat migrating dye, by a thermal head to heat migrating transfer the dye onto a heat transfer image-receiving material.

Since in the latter heat migrating transfer system, the transferring amount of dye can be changed by changing the energy applied to the thermal head, a gradation record (continuous tone record) can be easily obtained and hence the latter system is particularly useful for full color recordings of high image quality.

However, there are various restrictions on the heat migrating dye being used in this system. Dyes meeting all the properties required are very few.

The properties required for the heat migrating dye include that (i) the dye has preferably suitable spectral characteristics for color reproduction, (ii) the dye can easily cause heat migrating, (iii) the dye has a strong resistance to light and heat, (iv) the dye has a strong resistance to various chemicals, (v) the dye does not readily reduce the sharpness, (vi) the images of the dye formed do not readily retransfer, (vii) the dye does not cause bleeding out, crystallization, or aggregation in an image-receiving material for a long period of time, (viii) a heat transfer dye providing material can be easily prepared using the dye, (ix) the dye does not cause crystallization or aggregation in the heat transfer dye providing material for a long period of time, etc.

Dyes which satisfy all the requirements are not known at present, but the pyrazoloazole series azomethine dyes described in JP-A-64-63194 have very good properties as a magenta dye.

However, even the foregoing dyes do not satisfy all the properties described above. As the result of various investigations, the inventors have learned about the substituents of the coupler moieties of a pyrazoloazole series azomethine dye and the properties of the heat migrating dye and have succeeded in accomplishing the present invention.

Pyrazoloazole series azomethine dyes, the coupler moieties of which are substituted with an aryl group or a heterocyclic group, are excellent in fastness and heat migrating property. But in many of these dyes, the absorption wave form is broader than that of a pyrazoloazole series azomethine dye, the coupler moiety of which is substituted by an alkyl group.

The inventors believe that if the broadness of the absorption wave form of the foregoing dye is corrected, the dye becomes an excellent heat migrating dye. Thus, the inventors have investigated the substituents of the aryl group and the heterocyclic group of the coupler moiety and the properties of the heat migrating dye.

It is known in the field of a silver salt photography that when in a pyrazoloazole series coupler substituted by an aryl group, the ortho-position of the bonded position of the aryl group is substituted by an alkoxy group, etc., the absorption of the dye formed by the reaction of the coupler with a color developing agent becomes sharper than that of a dye originating from a coupler having no substituent at the orthoposition.

However, it was believed that the foregoing fact could not be applied to a heat migrating dye. First, it was anticipated that by newly introducing a substituent, the molecular weight was increased to reduce the heat migrating property. Second, if a substituent having a high electrical negativity, such as a halogen atom, a hetero atom, etc., is newly introduced, there were apprehensions that the electrostatic interaction between dyes would become large and cause the aggregation, deposition, and crystallization of the dyes in the dye-providing material and the image-receiving layer after heat transfer of the dyes. Third, it was expected that by the introduction of a new substituent, the interaction between the binder molecule and the dye in the dye-providing material and the image-receiving layer would be increased, resulting in an increase of the heat migrating property of the dye in the dye providing material.

As the result of various investigations, the inventors have found that contrary to the foregoing expectations, in the dyes in which the substituent of the coupler moiety is an aryl group or a heterocyclic group, the pyrazoloazole series azomethine dyes having the substituent at the ortho-position of the bonded position are excellent in their heat migrating property and solubility of the dyes in a solvent at the time of preparation of an ink, as compared with the dyes having no substituent at the ortho-position.

Furthermore, it has been found that a dye having a substituent at the ortho-position does not readily cause aggregation, deposition, crystallization, bleed out, etc., for a long period of time in the dye providing material or the image-receiving layer after transfer as, compared to the dyes having no substituent at the ortho-position. In addition, in the case of the dye having the substituent at the ortho-position, the occurrence of retransfer of dye images and blurring of dye images are reduced. These discoveries are utterly unexpected.

By these unexpected discoveries, it has become possible to invent pyrazoloazole series azomethine dyes substituted by an aryl group or a heterocyclic group at the ortho-position having a sharpened absorption waveform without reducing the properties required for a heat migrating dye.

European Patent 284,239 and JP-A-63-231341 (the term "JP-A" as used herein means an "unexamined published Japanese patent application") describe pyrazoloazole couplers being used for silver halide color photographic materials. That is, the dye formed from a pyrazoloazole coupler wherein one carbon atom directly bonded to the pyrazoloazole nucleus is included in an aryl group or a heterocyclic group and the coupler has an alkyl group, an alkoxy group or a halogen atom at at least one ortho-position of the carbon atom migrates the absorption maximum to a short wave side, reduces the half value width, and increases the light-fastness.

However, the present invention is not restricted by the foregoing disclosure of the patents.

A photographic coupler is a compound which is fixed in an oil droplet in a form which is hard to diffuse and becomes a dye by reacting with a color developing agent. Also, the structure of a coupler is designed so that the coupler and a dye formed from the coupler do not diffuse from the photographic layer in each step of development, bleach, fix, or wash.

Accordingly, it is impossible to anticipate the heat migrating property of the dye in the present invention from the foregoing disclosures of the patents about the coupler, the diffusion of which is prevented.

Furthermore, the foregoing couplers have a ballast group (non-diffusible group). The ballast group also functions as an oil-solubilizing group, whereby the couplers can dissolve well in oil droplets. That is, the solubility of the compound formed by removing the ballast group from the foregoing coupler compound is unknown and hence it can not be anticipated from the disclosures of the foregoing patents what the states of aggregation, crystallization, and deposition, and the ink aptitude of the compounds of the present invention would be in the dye providing material and the image-receiving layer. Moreover, JP-A-64-48863 describes a pyrazolotriazole series azomethine dye wherein the substituent of the coupler moiety is an ortho-acylaminophenyl group or an ortho-sulfonylaminophenyl group.

However, the present invention is not restricted by the dye described in the foregoing patent application.

Specifically, there is no description in the foregoing patent application of the heat migrating property, the solubility, the crystallinity, etc., of the foregoing dye. Further, there is no description of the change of the absorption based on the type of the substituent at the ortho-position of the aryl group.

Furthermore, the dyes described in the foregoing patent application are cyan dyes, which have no relation with the compounds of the present invention, which are used mainly as magenta dyes.

In other words, it is impossible to anticipate the heat migrating property and occurrence of the aggregation of the compounds in the materials of the present invention from the descriptions of the above-described patent application.

SUMMARY OF THE INVENTION

An object of this invention is, therefore, to provide a heat transfer dye providing material using a dye having an excellent heat migrating property and being excellent in the solubility of the dye during the preparation of an ink.

Other object of this invention is to provide a heat transfer dye providing material containing a dye which does not readily cause aggregation, deposition, crystallization, bleed out, etc., for a long period of time in the dye providing material or the image-receiving layer after transfer.

Still other object of this invention is to provide a heat transfer dye providing material containing a dye which does not readily cause the retransfer and blurring of the dye images formed with the passage of time.

A further object of this invention is to provide a heat transfer dye providing material containing a dye having a sharp absorption.

Other object of this invention is to provide a heat transfer dye providing material containing a dye which is excellent in fastness to light, heat, etc.

Still other objects of this invention will become apparent from the description of the specification.

It has now been discovered that the foregoing objects can be achieved by the present invention described hereinbelow.

According to the present invention, there is provided a heat transfer dye providing material comprising a support having thereon a dye providing layer containing a heat migrating dye, wherein the dye providing layer contains a compound represented by following formula (I):

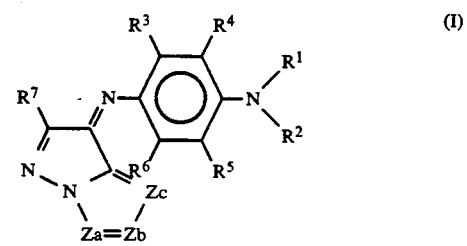

wherein $R^1$ and $R^2$ each independently represents a hydrogen atom, an alkyl group, an aryl group, or a heterocyclic group; $R^3$, $R^4$, $R^5$, $R^6$, and $R^7$ each independently represents a hydrogen atom or a non-metallic substituent; Za, Zb, and Zc each independently represents —N= or

(wherein $R^8$ represents a hydrogen atom or a non-metallic substituent), at least one of $R^7$ and $R^8$ is an aryl group or a heterocyclic group having a substituent at an ortho-position to the position bonded to the nitrogen-containing ring of formula (I); said $R^3$ and $R^4$, said $R^4$ and $R^1$, said $R^1$ and $R_2$, said $R^2$ and $R^5$, and/or said $R^5$ and $R^6$ may combine with each other to form a ring structure.

DETAILED DESCRIPTION OF THE INVENTION

Figure 1:
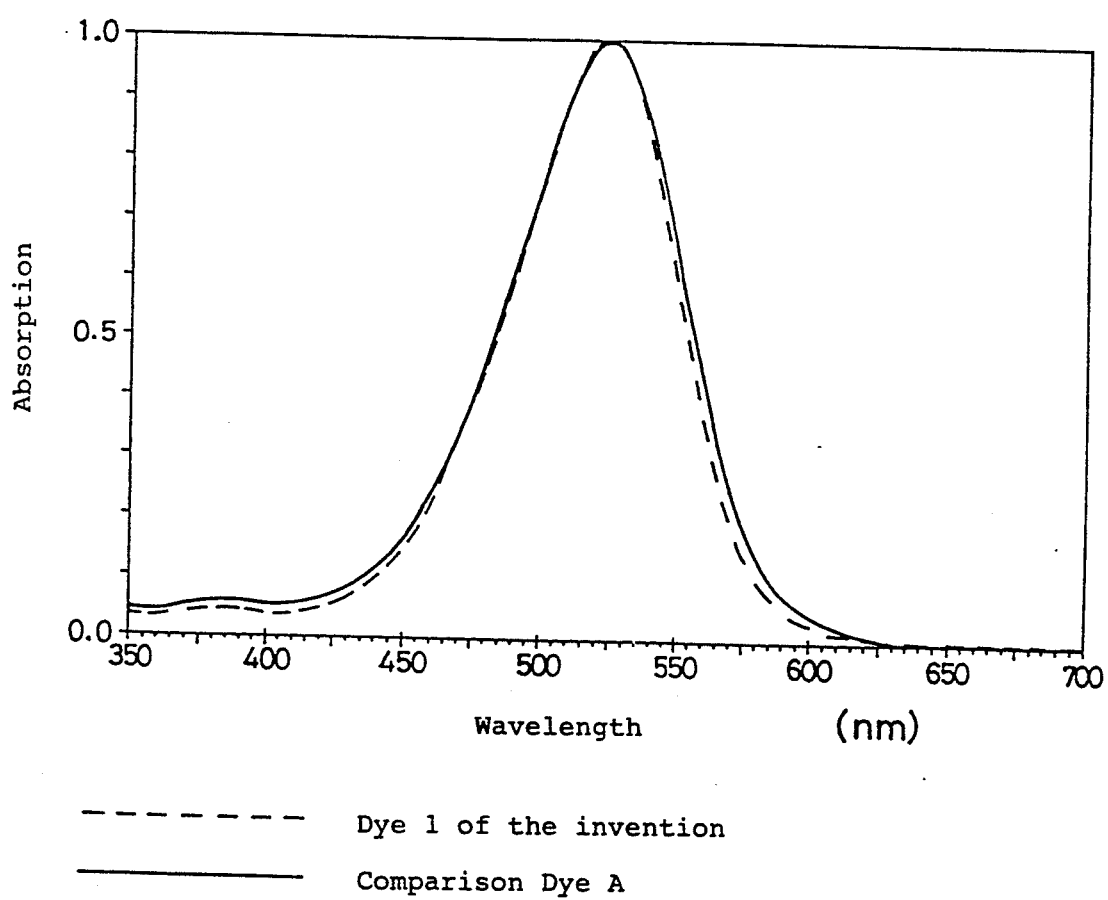
FIG. 1 is a graph showing the absorption characteristics of Dye 1 of this invention and Comparison Dye A in ethyl acetate (the absorption of $\lambda_{max}$ is defined as 1), wherein the broken line stands for the absorption characteristics of Dye 1 in this invention and the solid line for Comparison Dye A.

The heat migrating dye shown by formula (I) for use in this invention is described in detail.

In formula (I), $R^1$ and $R^2$ each independently represents a hydrogen atom, an alkyl group, an aryl group, or a heterocyclic group, and is preferably a hydrogen atom, an alkyl group (having from 1 to 12 carbon atoms, including substituted alkyl groups, e.g., methyl, ethyl, isopropyl, butyl, cyclopentyl, cyclohexyl, 2-methoxyethyl, 2-chloroethyl, 2-hydroxyethyl, 2-cyanoethyl, cyanomethyl, 2-methylsulfamoylethyl, 2-methylsulfonylaminoethyl, 2-methoxycarbonylethyl, 2-acetoxyethyl, methoxycarbonylmethyl, benzyl, and allyl), an aryl group (having from 6 to 12 carbon atoms, including substituted aryl groups, e.g., phenyl, p-tolyl, and m-chlorophenyl), of a heterocyclic group (having from 4 to 12 carbon atoms, including substituted heterocyclic groups, e.g.,

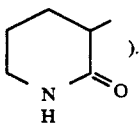

).

R$^1$ and R$^2$ each is most preferably an alkyl group having from 1 to 6 carbon atoms, which may be substituted.

Also, R$^1$ and R$^2$ may combine with each other to form a ring, e.g.,

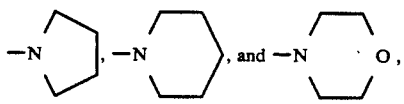

and further R$^1$ and R$^4$ and/or R$^2$ and R$^5$ may combine with each other to form a ring. Preferred examples of the ring are

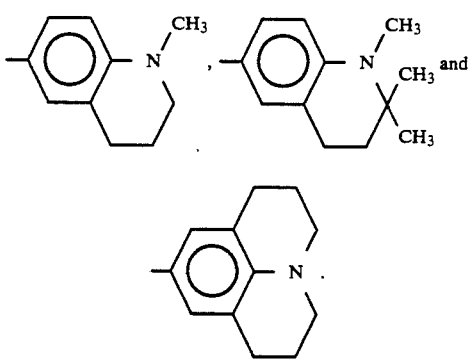

In formula (I), R$^3$, R$^4$, R$^5$, R$^6$, and R$^7$ each independently represents a hydrogen atom or a non-metallic atomic group and is preferably a hydrogen atom, an alkyl group, an alkoxy group, an aryloxy group, a halogen atom, an acylamino group, a cyano group, an alkoxycarbonylamino group, an aryloxycarbonylamino group, an aminocarbonylamino group, a sulfonylamino group, a carbamoyl group, a sulfamoyl group, an aryl group, an alkylthio group, an arylthio group, a sulfonyl group an acyl group, an amino group, or a heterocyclic group.

Examples thereof include a hydrogen atom, an alkyl group having from 1 to 12 carbon atoms, including substituted alkyl groups (e.g., methyl, ethyl, isopropyl, butyl, methoxyethyl, cyclohexyl, and phenethyl), an alkoxy group having from 1 to 12 carbon atoms, including substituted alkoxy groups (e.g., methoxy, ethoxy, isopropoxy, and methoxyethoxy), an aryloxy group having from 6 to 12 carbon atoms, including substituted aryloxy groups (e.g., phenoxy, p-methoxyphenoxy, p-chlorophenoxy, and p-methylphenoxy), a halogen atom (e.g., fluorine, chlorine, and bromine), an acylamino group [such as an alkylcarbonylamino group having from 1 to 10 carbon atoms, including substituted ones (e.g., formylamino, acetylamino, propionylamino, isobutyrylamino, hexahydrobenzoylamino, pivaloylamino, trifluoroacetylamino, hepta-fluorobutyrylamino, chloropropionylamino, cyanoacetylamino, and phenoxyacetylamino), a vinylcarbonylamino group having from 3 to 10 carbon atoms, including substituted ones (e.g., acryloylamino, methacryloylamino, and crotonoylamino), an arylcarbonylamino group having from 7 to 15 carbon atoms, including substituted ones (e.g., benzoylamino, p-toluylamino, pentafluorobenzoylamino, o-fluorobenzoylamino, m-methoxybenzoylamino, p-trifluoromethylbenzoylamino, 2,4-dichlorobenzoylamino, p-methoxycarbonylbenzoylamino, and 1-naphthoylamino), a heterylcarbonylamino group having from 5 to 13 carbon atoms, including substituted ones (e.g., picolinoylamino, nicotinoylamino, pyrrole 2-carbonylamino, thiophene-2-carbonylamino, furoylamino, and piperidine-4-carbonylamino), etc.], a cyano group, an alkoxycarbonyl group having from 2 to 10 carbon atoms, including substituted ones (e.g., methoxycarbonylamino, ethoxycarbonylamino, isopropoxycarbonylamino, methoxyethoxycarbonylamino, N-methylmethoxycarbonylamino, t-butoxycarbonylamino, and hexyloxycarbonylamino), an aryloxycarbonylamino group having from 7 to 15 carbon atoms, including substituted ones (e.g., phenoxycarbonylamino and o-chlorophenoxycarbonylamino), an aminocarbonylamino group having from 1 to 10 carbon atoms, including substituted ones (e.g., methylaminocarbonylamino, diemthylaminocarbonylamino, and butylaminocarbonylamino), a sulfonylamino group having from 1 to 10 carbon atoms (e.g., methanesulfonylamino, ethanesulfonylamino, N-methylmethanesulfonylamino, and phenylsulfonylamino), a carbamoyl group [such as an alkylcarbamoyl group having from 1 to 12 carbon atoms, including substituted ones (e.g., methylcarbamoyl, dimethylcarbamoyl, butylcarbamoyl, isopropylcarbamoyl, t-butylcarbamoyl, cyclopentylcarbamoyl, cyclohexylcarbamoyl, allylcarbamoyl, methoxyethylcarbamoyl, chloroethylcarbamoyl, cyanoethylcarbamoyl, ethylcyanoethylcarbamoyl, benzylcarbamoyl, ethoxycarbonylmethylcarbamoyl, furfurylcarbamoyl, tetrahydrofurfurylcarbamoyl, and phenoxymethylcarbamoyl), an arylcarbamoyl group having from 7 to 15 carbon atoms, including substituted ones (e.g., phenylcarbamoyl, p-toluylcarbamoyl, m-methoxyphenylcarbamoyl, 4,5-dichlorophenylcarbamoyl, p-cyanophenylcarbamoyl, p-acetylaminophenylcarbamoyl, p-methoxycarbonylphenylcarbamoyl, m-trifluoromethylphenylcarbamoyl, o-fluorophenylcarbamoyl, and 1-naphthylcarbamoyl), a heterylcarbamoyl group having from 4 to 12 carbon atoms, including substituted ones (e.g., 2-pyridylcarbamoyl, 3-pyridylcarbamoyl, 4-pyridylcarbamoyl, 2-thiazolylcarbamoyl, 2-benzthiazolylcarbamoyl, 2-benzimidazolylcarbamoyl, 2-(4-methylpyridylcarbamoyl, and 2-(5-methyl)-1,3,4-thiadiazolylcarbamoyl), etc.], a sulfamoyl group having from 0 to 12 carbon atoms (e.g., methylsulfamoyl, dimethylsulfamoyl, butylsulfamoyl, and phenylsulfamoyl), an aryl group including substituted ones (e.g., phenyl, p-tolyl, p-methoxyphenyl, and p-chlorophenyl), an alkylthio group including substituted ones (e.g., methylthio and butylthio), an arylthio group including substituted ones (e.g., phenylthio and p-tolylthio), a sulfonyl group (e.g., methanesulfonyl, butanesulfonyl, and phenylsulfonyl), an acyl group (e.g., acetyl, n-butyryl, and t-butyryl), an amino group (e.g., methylamino, dimethylamino, and anilino), and a heterocyclic group having from 2 to 9 carbon atoms.

Among the foregoing substituents shown by $R^3$, $R^4$, $R^5$, and $R^6$, a hydrogen atom, an alkyl group, an alkoxy group, an alkoxycarbonylamino group, an aminocarbonyl group, an acylamino group, and a sulfonylamino group are preferred.

In these groups, $R^3$ is more preferably a hydrogen atom, an alkyl group, an alkoxycarbonylamino group, an aminocarbonylamino group, or an acylamino group.

Among the groups shown by $R^4$, $R^5$, and $R^6$, a hydrogen group is most preferred.

$R^7$ is preferably an alkyl group (having from 1 to 8 carbon atoms), an aryl group (having from 6 to 12 carbon atoms), a heterocyclic group (having from 2 to 9 carbon atoms), an alkoxy group (having from 1 to 6 carbon atoms), or an aryloxy group (having from 6 to 12 carbon atoms).

Among the heat migrating dyes shown by foregoing formula (I), the dyes shown by following formulae (II), (III), (IV), (V), (VI), or (VII) are more preferred:

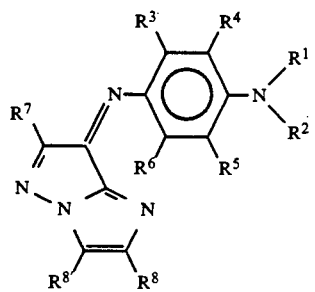
(II)

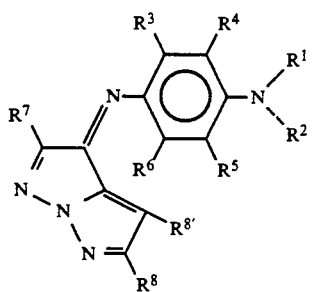
(III)

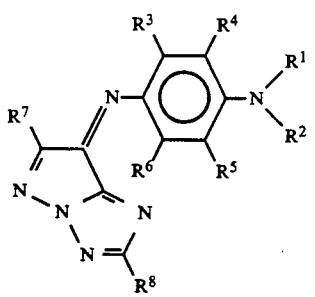
(IV)

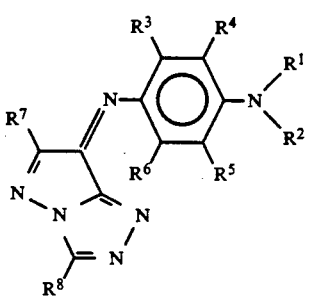
(V)

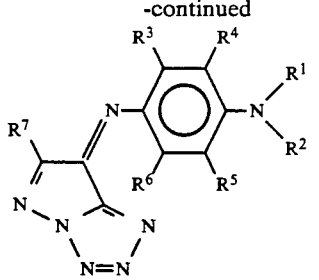
(VI)

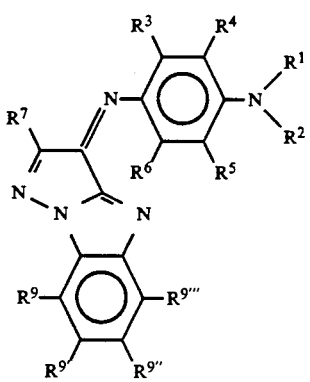
(VII)

In the above formulae, $R^8$ and $R^{8'}$ each represents a hydrogen atom or a non-metallic substituent and $R^9$, $R^{9'}$, $R^{9''}$, and $R^{9'''}$ are same as those shown by $R^3$, $R^4$, $R^5$, and $R^6$. Also, $R^1$, $R^2$, $R^3$, $R^4$, $R^5$, $R^6$, and $R^7$ are same as in formula (I) described above.

Among the dyes shown by formulae (II), (III), (IV), (V), (VI), and (VII), the dyes shown by formulae (IV) and (V) are more preferred.

$R^8$ represents a hydrogen atom or a non-metallic substituent as described above and is preferably a hydrogen atom, an alkyl group, an aryl group, a heterocyclic group, an alkoxy group, an amino group, an alkoxycarbonyl group, or an acyl group.

Among these groups, an alkyl group (having from 1 to 12 carbon atoms and including substituted ones), an aryl group (having from 6 to 12 carbon atoms), and a heterocyclic group (having from 2 to 10 carbon atoms) are more preferable.

Examples of the alkyl group are t-butyl, i-propyl,

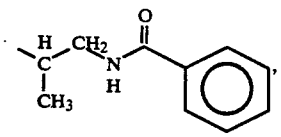

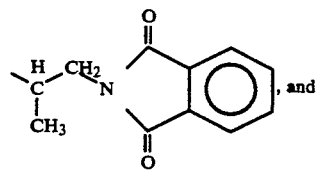
, and

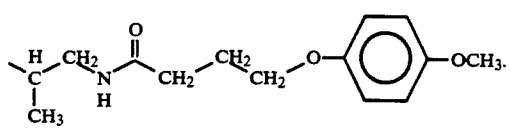

Examples of the aryl group are a phenyl gorup,

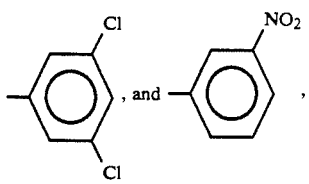

and specific examples of a heterocyclic group are

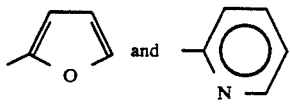

In formula (I), at least one of $R^7$ and $R^8$ is an an aryl group of a heterocyclic group each having a substituent at the ortho-position of the bonded position.

This aryl group or heterocyclic group is represented by following formula (VIII):

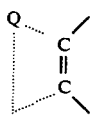 (VIII)

wherein Q represents an atomic group necessary for forming an aryl group or a heterocyclic group and $R^{10}$ represents a substituent.

The group shown by formula (VIII) described above is more preferably the group shown by following formulae (IX), (X), (XI), (XII), (XIII), (XIV), (XV), (XVI), (VII), or (XVIII):

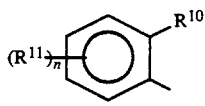 (IX)

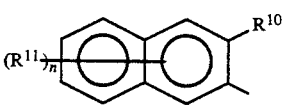 (X)

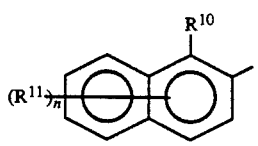 (XI)

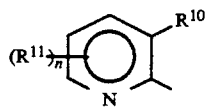 (XII)

 (XIII)

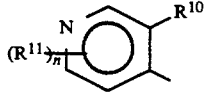 (XIV)

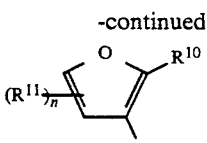 (XV)

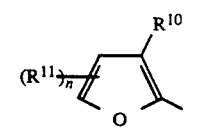 (XVI)

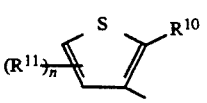 (XVII)

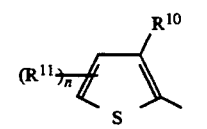 (XVIII)

In the above formulae, $R^{10}$ and $R^{11}$ each represents a substituent and have the same meaning as $R^3$, $R^4$, $R^5$, and $R^6$, and practical examples thereof are also same as for these groups; and n represents an integer.

If $R^{10}$ is a hydrogen-bonding group, the ransfer property is undesirably lowered. $R^{10}$ is preferably chlorine, bromine, an alkyl group having from 1 to 12 carbon atoms (e.g., methyl, ethyl, isobutyl, and t-butyl), an alkoxy group having from 1 to 12 carbon atoms (e.g., methoxy, ethoxy, n-butoxy, isopropoxy, and methoxyethoxy), or an aryloxy group having from 6 to 12 carbon atoms (e.g., phenoxy and p-methoxyphenoxy). $R^{10}$ is most preferably a chlorine atom or an alkoxy group (having from 1 to 6 carbon atoms).

$R^{11}$ is preferably a hydrogen atom or the groups described above as preferred ones of $R^{10}$.

Examples of the group shown by formula (VIII) include:

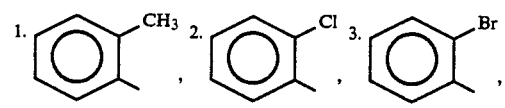

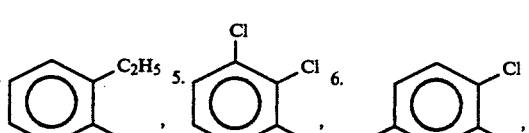

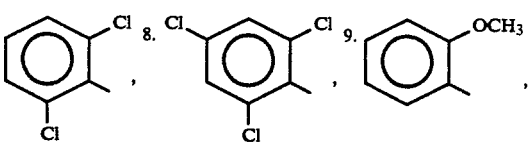

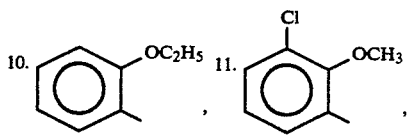

-continued

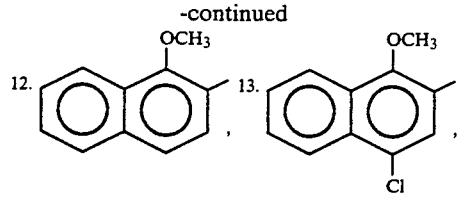

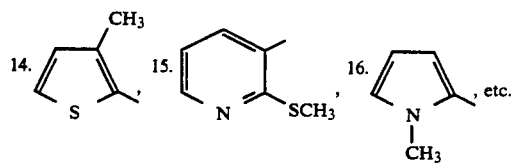

The dye for use in this invention may have an atomic group having the effect of restraining fading, in the molecule of the dye. This is particularly desirable when the color images formed are required to have a high fastness.

The atomic group having the effect of restraining fading may bonded to any site such as $R^1$, $R^2$, $R^3$, $R^4$, $R^5$, $R^6$, $R^7$, Za, Zb, and Zc, of the dye.

As the atomic group having the effect of restraining fading, the atomic groups described in European Patent 423,796A can be all used.

Examples of the atomic group having the effect of restraining fading are illustrated below but the invention is not limited thereby:

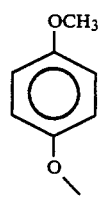

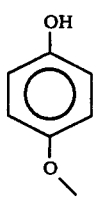

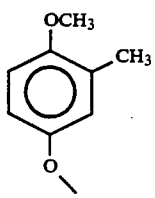

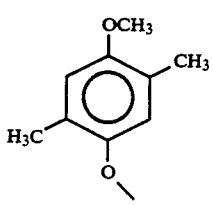

-continued

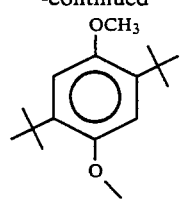

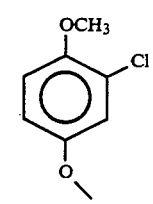

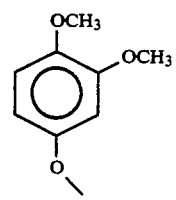

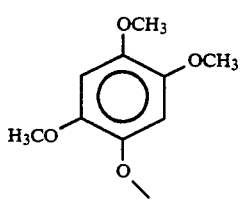

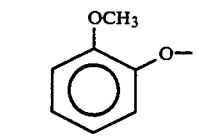

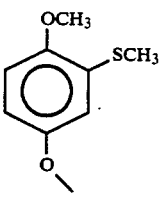

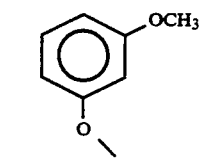

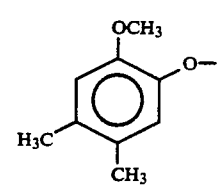

-continued
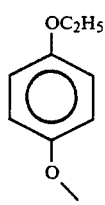
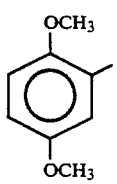
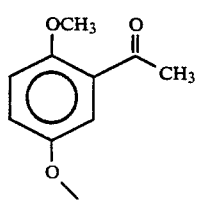
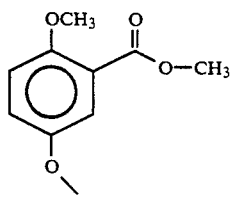
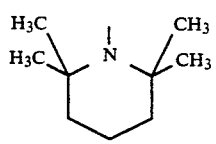
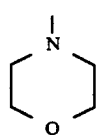
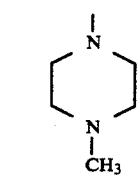
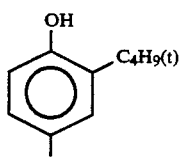
-continued
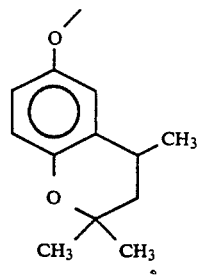
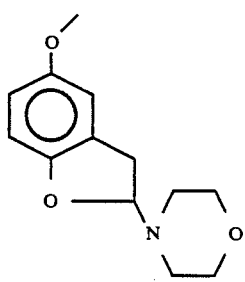
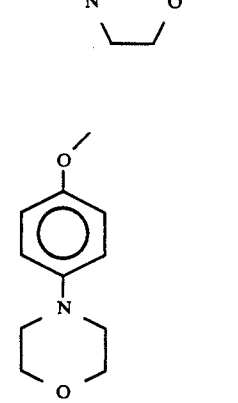
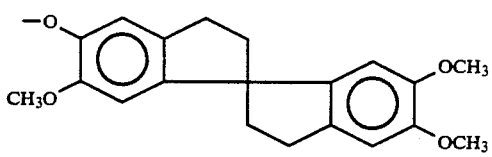
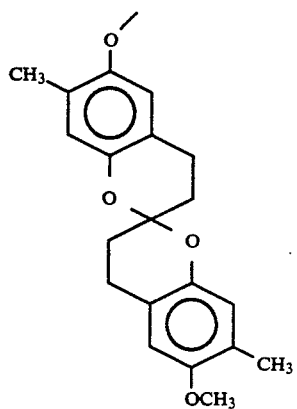

-continued
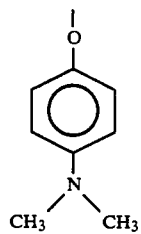
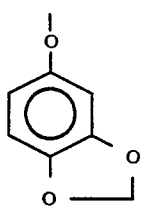
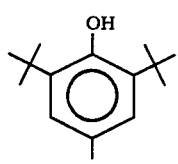
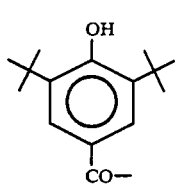
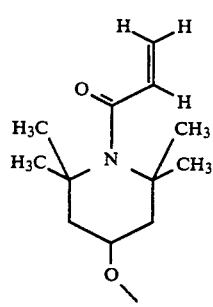
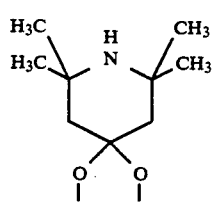
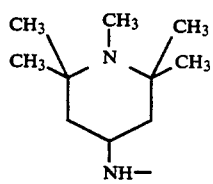
-continued
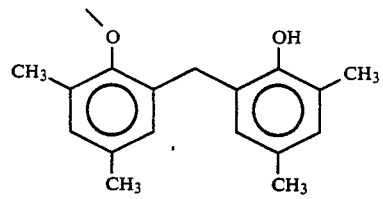
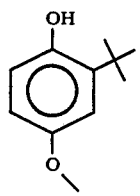
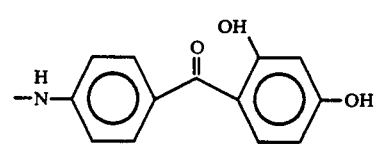
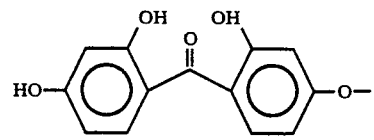
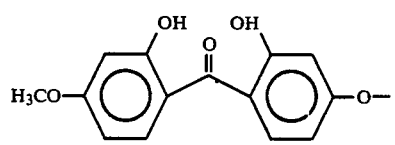
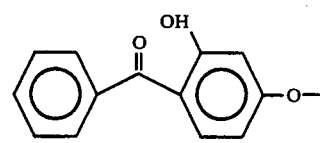
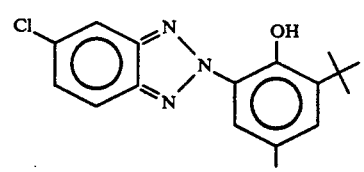
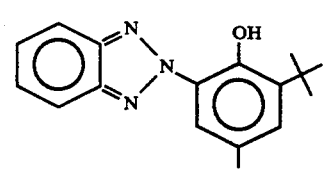
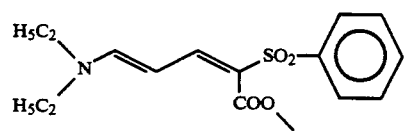

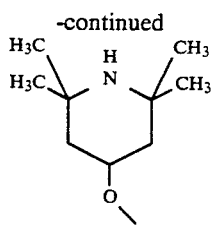
Then, specific examples of the heat migrating dye represented by formula (I) for use in this invention are illustrated below, but the invention is not limited to them:
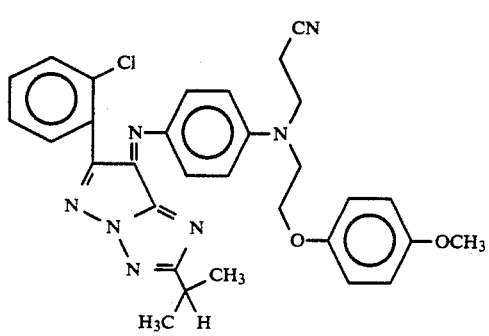
1.
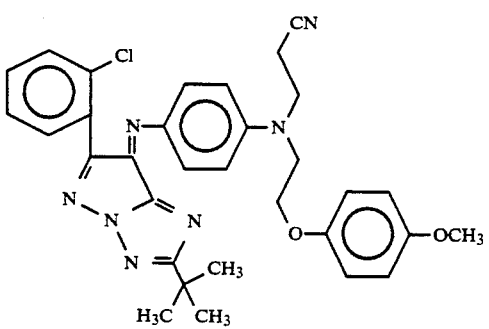
2.
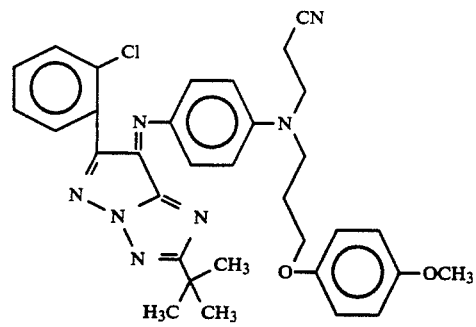
3.
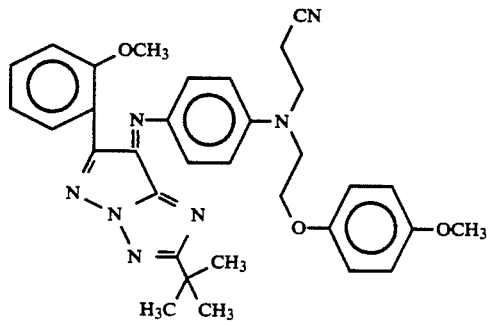
4.
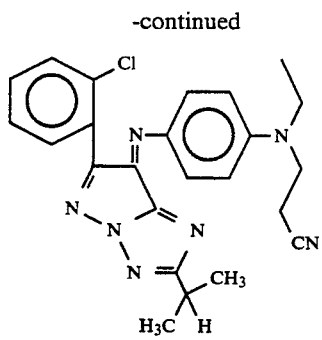
5.
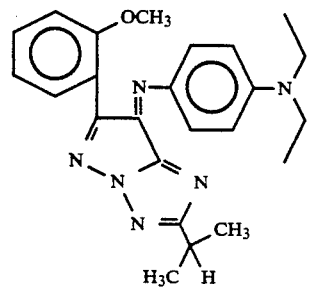
6.
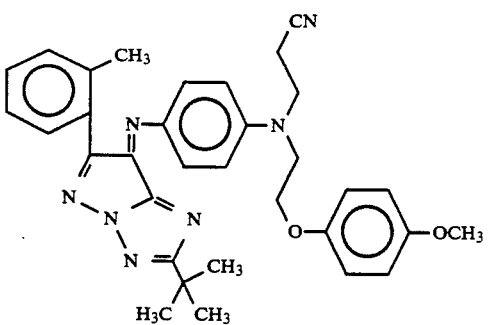
7.
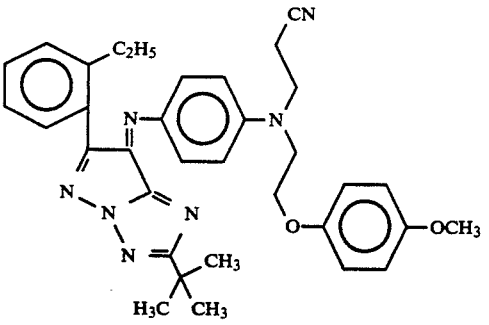
8.
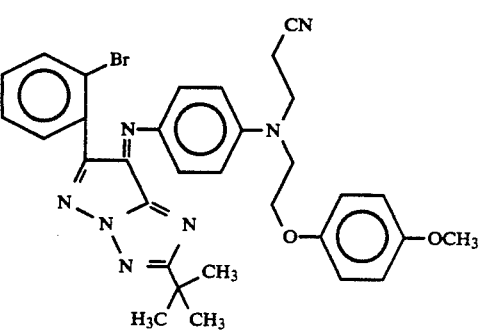
9.

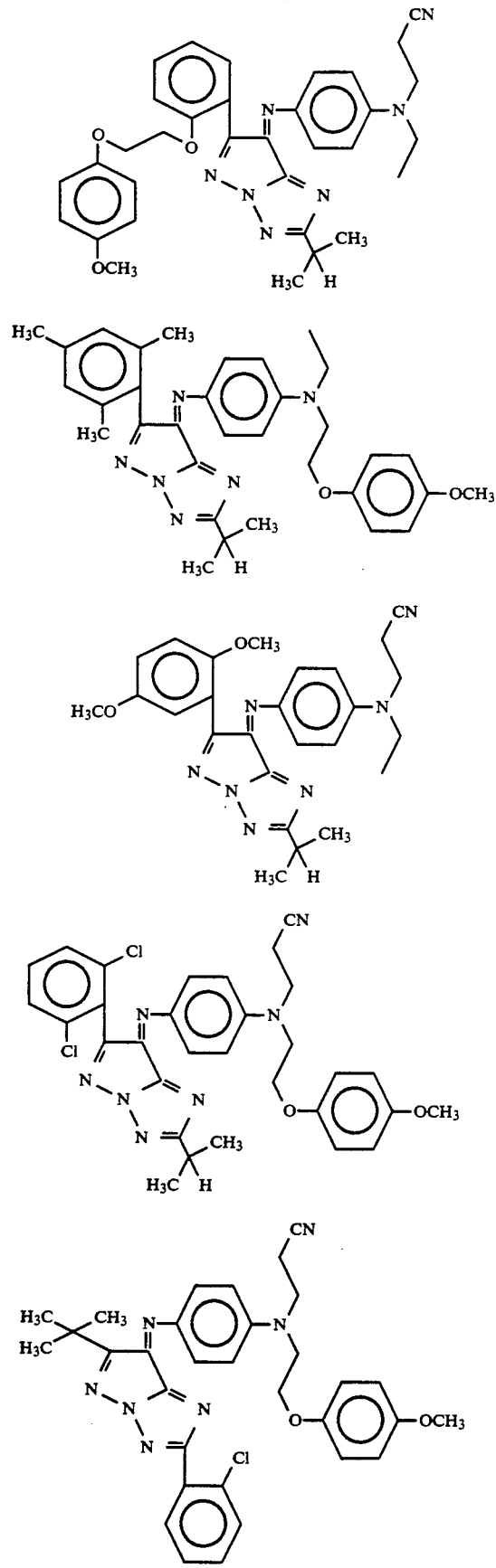

19.
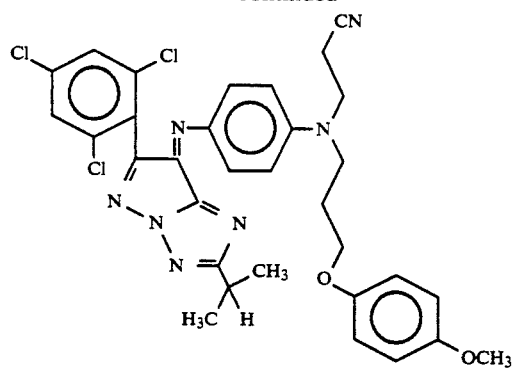
20.
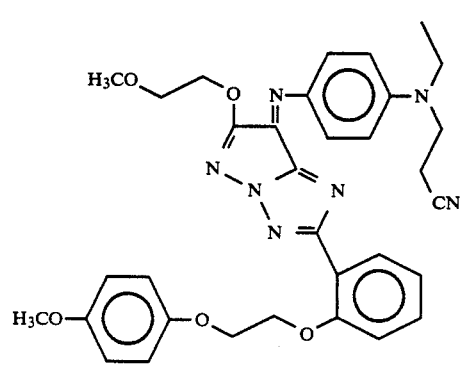
21.
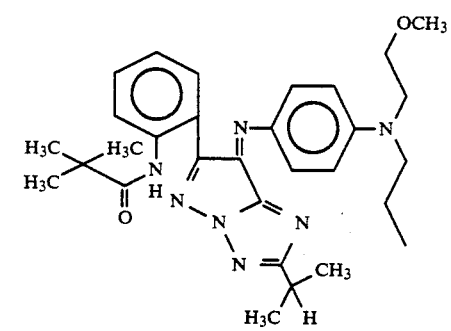
22.
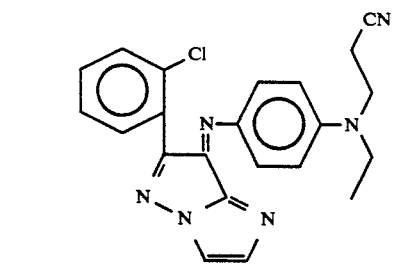
23.
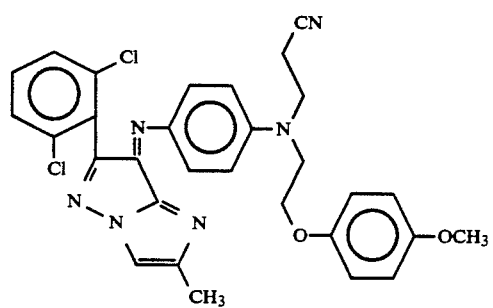
24.
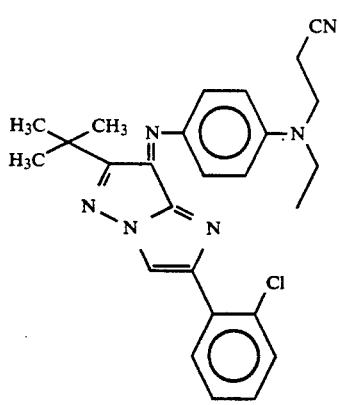
25.
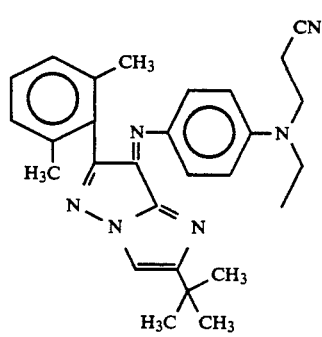
26.
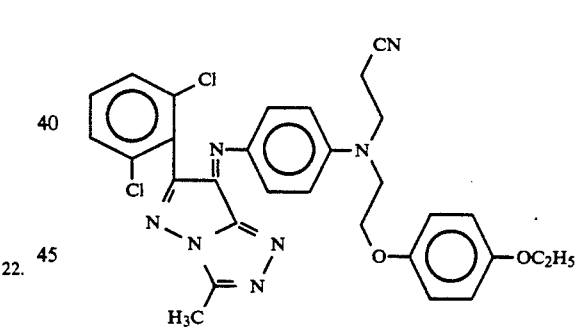
27.
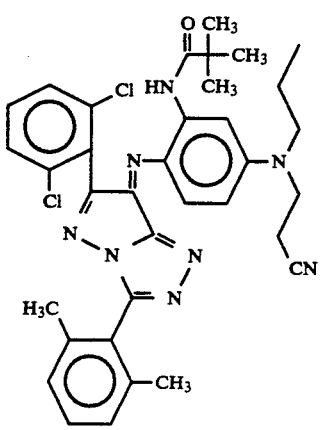

28.
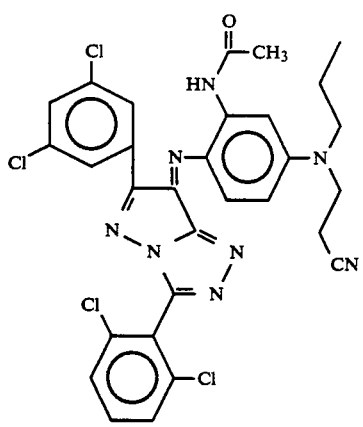
29.
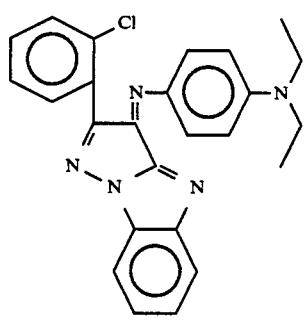
30.
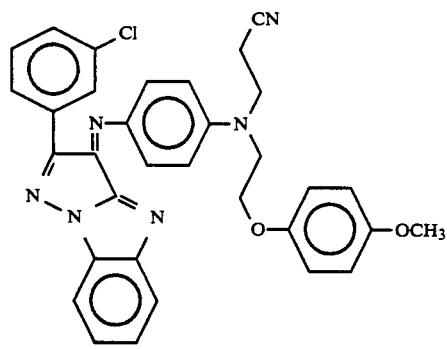
31.
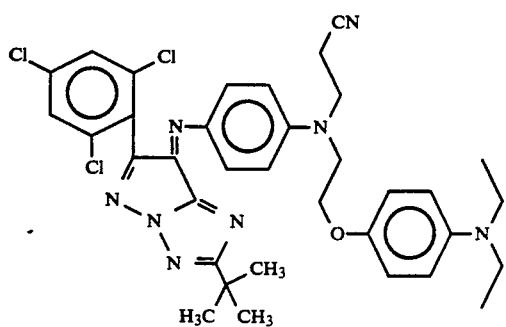
32.
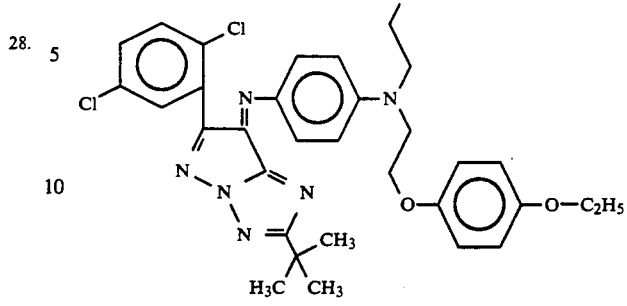
33.
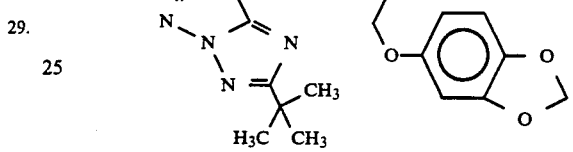
34.
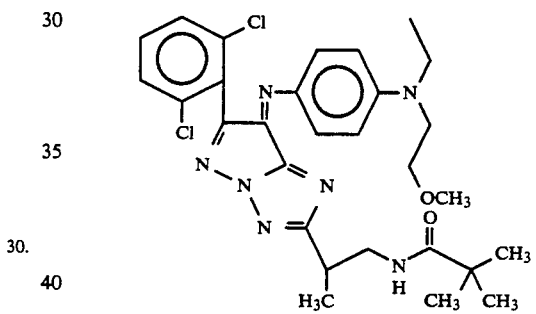
35.
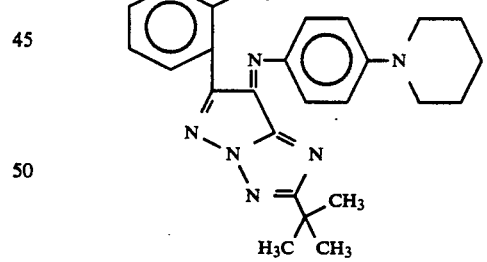
36.
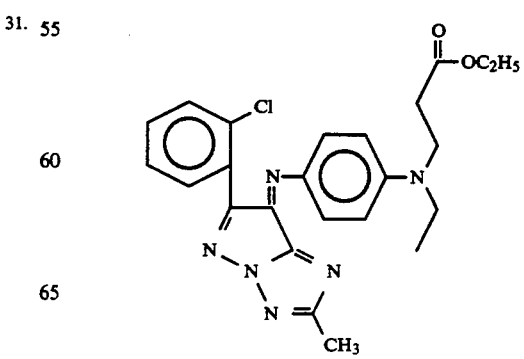

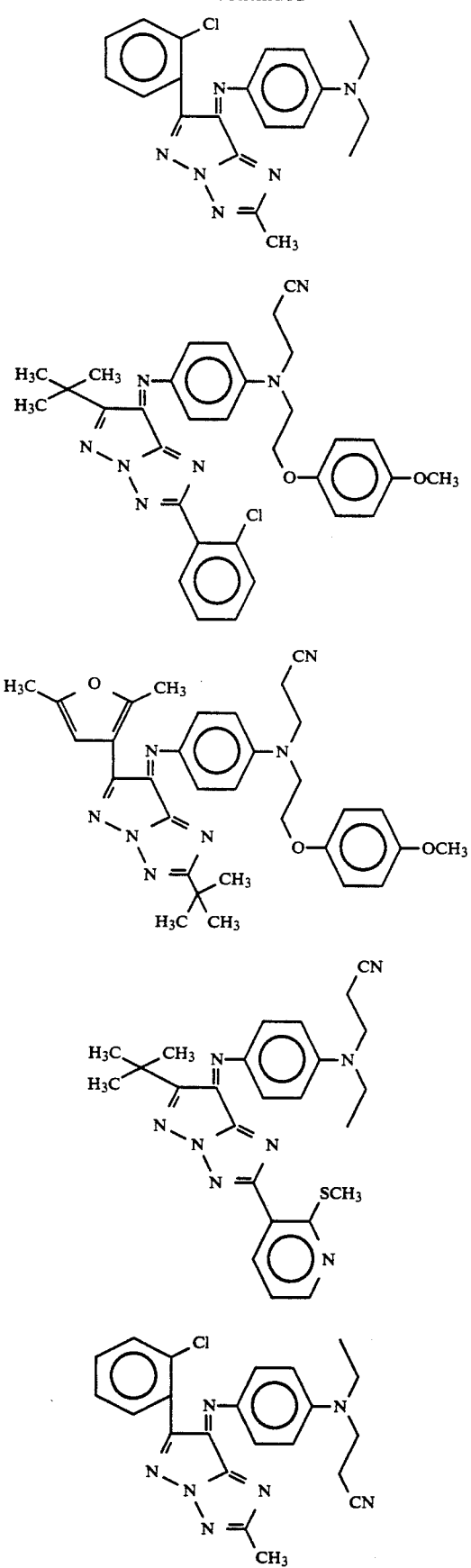

-continued

47. 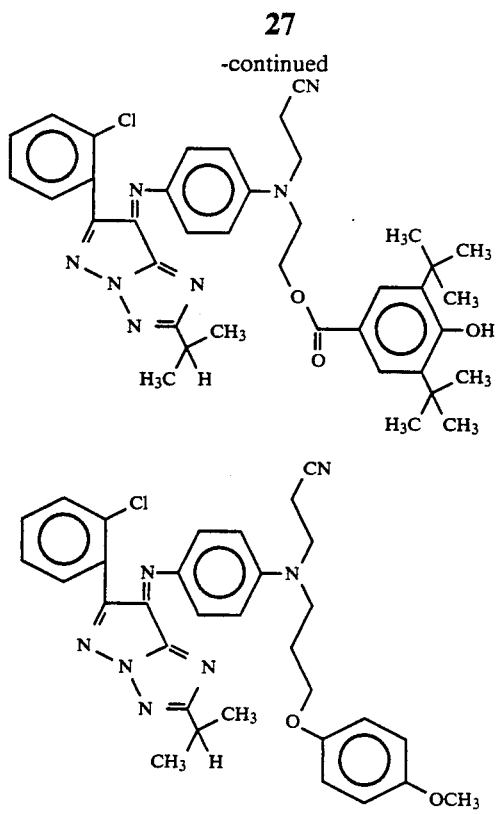

48.

The heat migrating dye shown by formula (I) for use in this invention is synthesized by oxidative coupling of coupler compound (a) shown by the following formula and coupler compound (b) shown by following formula.

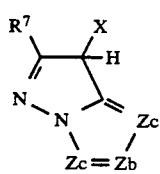

Coupler (a)

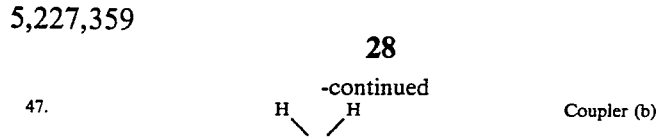

Coupler (b)

In the formulae, X represents a hydrogen atom or a releasable group which releases during the coupling reaction, and $R^1$, $R^2$, $R^3$, $R^4$, $R^5$, $R^6$, $R^7$, Za, Zb, and Zc are as defined as in formula (I).

Compound (a) is not only a compound having the above structure but also may be a tautomer thereof.

In another method of obtaining the dye for use in this invention, the dye is synthesized by dehydro-condensing coupler (a), wherein X is a hydrogen atom, and coupler compound (c) shown below.

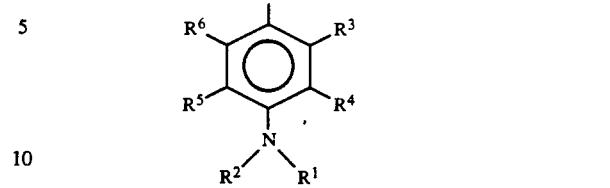

Coupler (c)

Synthesis examples of the dyes shown by formula (I) are shown below:

SYNTHESIS EXAMPLE 1—Synthesis of Dye 1

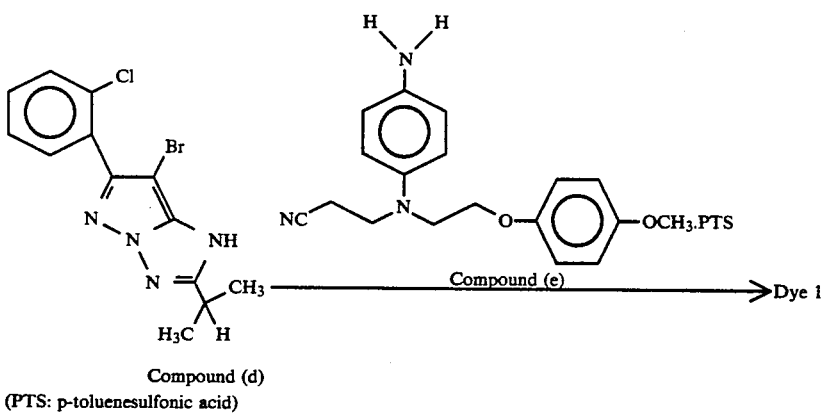

(PTS: p-toluenesulfonic acid)

While stirring a mixture of 21 g of Compound (d), 420 ml of methylene chloride, 210 ml of ethyl acetate, and 140 ml of ethanol at room temperature, a solution of 51 of sodium carbonate dissolved in 210 ml of water was added to the mixture. Thereafter, a solution of 44 g of sodium persulfate dissolved in 84 ml of water was added thereto. Thereafter, 43 g of Compound (e) was slowly added intermittently over a period of one hour.

Thereafter, the reaction was carried out for one hour at room temperature, and an organic layer formed was collected, washed twice with water, and dried using magnesium sulfate. After filtering, the solvent was distilled off under reduced pressure from the filtrate.

The crude reaction product thus obtained was purified using a silica gel chromatography (chloroform: ethyl acetate=20:1), and the purified product was recrystallized from a mixture of ethyl acetate and methanol (1:2) to provide 12.6 g of Dye 1. (Yield: 70%, melting point: 176° to 177° C.)

SYNTHESIS EXAMPLE 2—SYNTHESIS OF DYE 48

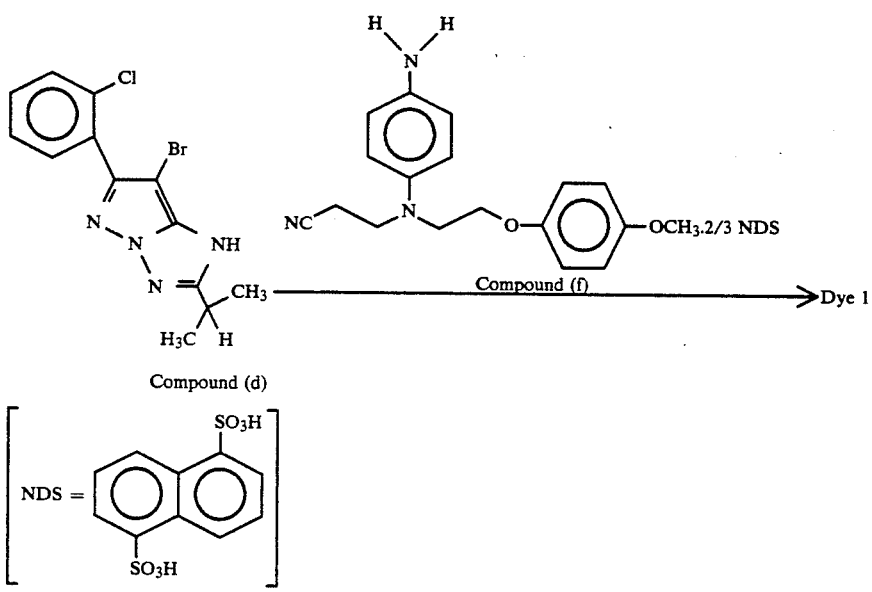

A mixture of 39 liters of methylene chloride, 1.75 kg (5.15 mols) of Compound (d), and 2.44 kg (24.1 mols) of triethylamine was stirred at 24° C. to dissolve completely the compound. After simultaneously adding thereto 1.00 kg (1.77 mols) of Compound (f) and 330 g (1.85 mols) of N-bromosuccinimide over a period of 10 minutes, the reaction was carried out for 5 minutes.

Furthermore, 1.00 kg (1.77 mols) of Compound (f) and 330 g (1.85 mols) of N-bromosuccinimide were further simultaneously added to the reaction mixture over a period of 10 minutes, and then the reaction was carried out for 5 minutes.

Thereafter, 15 liters of water was added to the reaction mixture. After stirring for 10 minutes, the reaction mixture was allowed to stand, and an aqueous layer thus formed was collected and washed with a solution of 1.0 kg of sodium chloride dissolved in 10 liters of water.

Thereafter, methylene chloride was distilled off under reduced pressure. The oily product thus obtained was dissolved in 3.5 liters of ethyl acetate. After heating the solution until the inside temperature became 55° C., 7.0 liters of methanol was added thereto. The mixture was allowed to cool with stirring, and when the inside temperature became 20° C., the mixture was filtered.

The crystals thus obtained were washed well with 2.0 liters of a mixed solvent of ethyl acetate and methanol (1:2) and then dried to provide 2.15 kg of Dye 48. (Yield: 72%, melting point: 149° to 150° C.).

In Synthesis Example 1 described above, when the same procedure was followed except that the same molar amount of ammonium persulfate was used in place of sodium persulfate, Dye 1 could be synthesized but in this case the yield was 36%.

The heat migrating dye for use in this invention is incorporated in a dye providing layer on a support to provide a heat transfer dye providing material, which is used for the image formation in a heat transfer system.

The heat migrating dye for use in this invention for the image formation in a heat transfer system is now explained in detail.

For forming a full color image, dyes of three colors, i.e., yellow, magenta, and cyan are usually necessary.

In regard to the formation of a particular color, the dye of this invention may be used together with a conventionally known dye. Also, two or more dyes in this invention forming the same color may be used as a mixture thereof.

The method of using the heat migrating dye in this invention is now explained.

A heat transfer dye providing material can be used in a sheet form, a continuous roll (web) form or ribbon form.

In this invention, each dye of yellow, magenta, or cyan is usually disposed on a support such that each dye forms each independent region. For example, a yellow dye region, a magenta dye region, and a cyan dye region are disposed on one support in the order of definite surface areas or in the order of long strip-form layers. Also, three kinds of heat transfer dye providing materials each composed of a support having formed thereon the layer of the foregoing yellow dye, magenta dye, or cyan dye are prepared, and the heat transfer of each dye can be successively applied onto one heat transfer image receiving material from the three heat transfer dye providing materials.

The heat migrating dye for use in this invention is dissolved or dispersed in a suitable solvent together with a binder and can be coated on a support, or can be printed on a support by a printing method such as a gravure method.

The thickness of the dye providing layer containing the foregoing dye is selected in the range of usually from about 0.2 μm to 5 μm, and particularly from 0.4 μm to 2 μm, as dry thickness.

The dye providing layer may be formed with one layer or may be formed with two or more layers for using a method of repeatedly using many times. In this case, the content of the dye and the ratio of dye/binder in each layer may differ.

The coating amount of the dye is preferably from 0.03 g/m² to 1 g/m², and more preferably from 0.1 g/m² to 0.6 g/m² of the surface area of the dye providing layer.

As the binder resin to be used with the aforesaid dyes, any binder resin conventionally known for such a purpose can be used. But usually binder resins which have a high heat resistance and which do not disturb the migration of the dye during heating are used.

Examples of the binder resin for use in this invention include a polyamide series resin, a polyester series resin, an epoxy resin, a polyurethane series resin, a polyacrylic resin (e.g., polymethyl methacrylate, polyacrylamide, and polystyrene-2-acrylonitrile), a vinyl series resin such as polyvinylpyrrolidone, a polyvinyl chloride series resin (e.g., a vinyl chloridevinyl acetate copolymer), a polycarbonate series resin, polystyrene, polyphenylene oxide, a cellulose series resin (e.g., methyl cellulose, ethyl cellulose, carboxymethyl cellulose, cellulose acetate hydrogen phthalate, cellulose acetate, cellulose acetate propionate, cellulose acetate butyrate, and cellulose triacetate), a polyvinyl alcohol series resin (e.g., polyvinyl alcohol and partially saponificated polyvinyl alcohol such as polyvinyl acetal, polyvinyl butyral, etc.), a petroleum series resin, rosin derivatives, a coumarone-indene series resin, a terpene series resin, and a polyolefin series resin (e.g., polyethylene and polypropylene).

In this invention, it is preferable that such a binder resin is used in a ratio of from about 20 to 600 parts by weight per 100 parts by weight of the dye.

As an ink solvent for dissolving or dispersing the foregoing dye and the binder resin, any conventionally known ink solvent can be used.

As the support for the heat transfer dye providing material, conventionally known supports can be used. Examples of the support are polyethylene terephthalate, polyamide, polycarbonate, a glassine paper, a condenser paper, a cellulose ester, a fluorine polymer, polyether, polyacetal, polyolefins, polyimide, polyphenylene sulfide, polypropylene, polysulfone, and cellophane.

The thickness of the support for the heat transfer dye providing material is generally from 2 μm to 30 μm. Also, if necessary, a subbing layer may be formed on the support. Also, a dye diffusion-preventing layer composed of a hydrophilic polymer may be formed between the support and the dye providing layer, whereby the transfer density is improved. As the hydrophilic polymer, the foregoing water-soluble polymer can be used.

For preventing a thermal head from sticking to the dye providing material, a slipping layer may be formed on the dye providing material. The slipping layer is composed of a lubricating material containing or not containing a polymer binder, such as a surface active agent, a solid or liquid lubricant, or a mixture thereof.

Furthermore, for preventing sticking of a thermal head during printing by heat from the back surface of the dye providing material and for improving sliding, it is better to apply a stick preventing treatment to the opposite side of the support to the side having the dye providing layer.

For example, it is preferable to form a heat resisting slip layer mainly composed of (1) a reaction product of a polyvinyl butyral resin and isocyanate, (2) an alkali metal salt or alkaline earth metal salt of a phosphoric acid ester. As the polyvinyl butyral resin, a resin having a molecular weight of from about 60,000 to 200,000 and a glass transition point of from 80° to 110° C. is preferred. Also, to have many reaction sites with isocyanate, a polyvinyl butyral resin having from 15 to 40% by weight a vinyl butyral moiety is preferred. As the alkali metal salt or alkaline earth metal salt of a phosphoric acid ester, Gafac RD720 (trade name, made by Toho Chemical Co., Ltd.), etc., are used. The alkali metal salt or alkaline earth metal salt is used in an amount of from 1 to 50% by weight, and preferably from about 10 to 40% by weight based on the amount of the polyvinyl butyral.

It is desirable that the heat resisting slip layer has a heat resisting layer as the lower layer. It is better to form a combination of a heat-curable synthetic resin and a curing agent thereof, e.g., a combination of polyvinyl butyral and a polyhydric isocyanate, a combination of acrylic polyol and a polyhydric isocyanate, a combination of cellulose acetate and a titanium chelating agent, or a combination of a polyester and an organotitanium compound by coating.

A hydrophilic dye barrier layer is sometimes formed on the dye providing material for preventing the diffusion of the dye in the support direction. The hydrophilic dye barrier layer contains a hydrophilic material useful for the intended purpose. In general, an excellent result is obtained by using gelatin, poly(acrylamide), poly(isopropylacrylamide), butyl methacrylate graft gelatin, ethyl methacrylate graft gelatin, cellulose monoacetate, methyl cellulose, poly(vinyl alcohol), poly(ethyleneimine), poly(acrylic acid), a mixture of poly(vinyl alcohol) and poly(vinyl acetate), a mixture of poly(vinyl alcohol) and poly(acrylic acid), or a mixture of cellulose monoacetate and poly acrylic acid) as the hydrophilic material.

In these materials, poly(acrylic acid), cellulose monoacetate, or poly(vinyl alcohol) are particularly preferable.

On the dye providing material may be formed a subbing layer. In this invention, any subbing layer may be employed if the subbing layer performs the desired function, but preferred examples include an (acrylonitrile-vinylidene chloride-acrylic acid) copolymer (14:80:6 by weight ratio), a (butyl acrylate-2-aminoethyl methacrylate-2-hydroxyethyl methacrylate) copolymer (30:20:50 by weight ratio), a linear/unsaturated polyester such as Bostick 7650 (trade name, made by M Haat Co., Bostic Chemical Group), and a chlorinated high-density poly(ethylene-trichloroethylene) resin.

There is no particular restriction on the coating amount of the subbing layer, but the coating amount is usually from 0.1 g m² to 2.0 g/m² of the dye provided material.

In this invention, the heat transfer dye providing material is superposed on the heat transfer image-receiving material, and by applying a heat energy corresponding to an image by a heating means such as a thermal head from any face of the assembly and preferably from the back surface of the heat transfer dye providing material, the dye in the dye providing layer can be transferred onto the heat transfer image-receiving material according to the amount of the heat energy. Color images having excellent sharpness and a resolving gradation can be obtained. Also, a fading inhibitor can be similarly transferred.

As the heating means, not only a thermal head but also other known means such as laser light (e.g., semiconductor laser), an infrared flash, a heat pen, etc., can be used.

In this invention, by combining the heat transfer dye providing material and the heat transfer image-receiving material, the system can be utilized to make prints of images by printing using various kinds of printers of a heat printing system, a facsimile system, a magnetic recording system, a magneto-optical recording system, an optical recording system, etc., or a print formation from a television or a CRT image.

Details of the heat transfer recording method are described in JP-A-60-34895.

The heat transfer image-receiving material which is used in combination with the heat transfer dye providing material of this invention comprises a support having formed thereon an image-receiving layer for receiving the dye migrating from the dye providing material. It is preferable that the image-receiving layer is a layer containing a material which is capable of receiving the heat migrating dye migrated from the heat transfer dye providing material either alone or together with another binder material and which has a thickness of from about 0.5 μm to 5.0 μm. Specific examples of the material (polymer) capable of receiving the heat migrating dye include the following resins:

(a) Resins having an ester bond

There are polyester resins obtained by obtaining the condensation product of a dicarboxylic acid component (the dicarboxylic acid component may have a sulfonic acid group, a carboxy group, etc., as a substituent), such as terephthalic acid, isophthalic acid, succinic acid, etc., and ethylene glycol, diethylene glycol, propylene glycol, neopentyl glycol, bisphenol A, etc.; polyacrylic acid ester resins or polymethacrylic acid ester resins such as polymethyl methacrylate, polybutyl methacrylate, polymethyl acrylate, polybutyl acrylate, etc.; polycarbonate resins; polyvinyl- acetate resins; styrene acrylate resins; vinyltoluene acrylate resins, etc. Practical examples of these resins are described in JP-A-59-101395, JP-A-63-7971, JP-A-63-7972, JP-A-63-7973, and JP-A-60-294862. Also, commercially available resins such as Vylon 290, Vylon 200, Vylon 280, Vylon 300, Vylon 103, Vylon GK-140, and Vylon GK-130 (trade names, made by Toyobo Co., Ltd.) and ATR-2009 and ATR-2010 (trade names, made by Kao Corporation) can be used.

(b) Resins having a urethane bond

There are polyurethane resins, etc.

(c) Resins having an amide bond

There are polyamide resins, etc.

(d) Resins having a urea bond

There are urea resins, etc.

(e) Resins having a sulfone bond

There are polysulfone resins, etc.

(f) Other resins having a bond of high polarity

There are polycaprolactone resins, styrene-maleic anhydride resins, polyvinyl chloride resins, polyacrylonitrile resins, etc.

In addition to the above-described synthetic resins, a mixture of these resins and copolymers can be used. The heat transfer image-receiving material, in particular the image-receiving layer, can further contain a high-boiling organic solvent or a heat solvent as a material capable of receiving the heat migrating dye or as a diffusion aid for the dye.

Practical examples of the high-boiling organic solvent and the heat solvent are described in JP-A-62-174754, JP-A-62-245253, JP-A-61-209444, JP-A-61-200538, JP-A-62-8145, JP-A-62-9348, JP-A-62-30247, and JP-A-62-136646.

The image-receiving layer of the heat transfer image-receiving material for use in this invention may be constituted to support the material capable of receiving the heat migrating dye as a dispersion in a water-soluble binder. As the water-soluble binder which is used in this case, various known water-soluble polymers are suitable, but a water-soluble polymer having a group capable of causing a crosslinking reaction by a hardening agent is preferably used.

The image-receiving layer may comprise two or more layers. In this case, it is desirable that for the layer near the support, a synthetic resin having a low glass transition point is used and a high-boiling organic solvent or a heat solvent is used for increasing the dyeing property for the dye. For the uppermost layer, a synthetic resin having a high glass transition point is used and a high-boiling organic solvent or a heat solvent is used in an amount as small as possible or is not used at all, whereby the occurrence of stickiness of the surface, sticking of the surface to other materials, retransfer of the dye to other materials after transfer, blocking with the heat transfer dye providing material, etc., is prevented.

The whole thickness of the image-receiving layer is preferably in the range of from 0.5 μm to 50 μm, and particularly from 3 μm to 30 μm. When the image-receiving layer is composed of two or more layers, the thickness of the outermost layer is preferably in the range of from 0.1 μm to 2 μm, and particularly from 0.2 μm to 1 μm.

The heat transfer image-receiving layer for use in this invention may have an interlayer between the support and the image-receiving layer.

The interlayer is a layer having the functions of a cushioning layer, a porous layer, and a diffusion prevention layer for the dye. And, as the case may be, the layer also functions as an adhesive layer.

The diffusion prevention layer of the dye has the function of preventing the heat migrating dye from diffusing into the support. As the binder constituting the diffusion preventing layer, a water-soluble binder or an organic solvent-soluble binder may be used. But a water-soluble binder is preferable, and examples thereof include the water-soluble binders illustrated above as the binder for the image-receiving layer, of which gelatin is particularly preferable.

The porous layer is a layer having the function of preventing heat applied at the heat transfer from diffusing from the image-receiving layer into the support to utilize effectively the applied heat.

The image-receiving layer, the cushioning layer, the porous layer, the diffusion prevention layer, the adhesive layer, etc., constituting the heat transfer image-receiving layer in this invention may contain a fine powder of silica, clay, talc, diatomaceous earth, calcium silicate, calcium sulfate, barium sulfate, aluminum silicate, synthetic zeolite, zinc oxide, lithopone, titanium oxide, alumina, etc.

As the support for the heat transfer image-receiving material in this invention, any support which can endure the transfer temperature and meets the requirements for smoothness, whiteness, sliding property, friction, antistatic property, depression resistance after transfer, etc., can be used.

Examples of the support include paper supports such as synthetic papers (e.g., polyolefin series synthetic papers, polystyrene series synthetic papers, etc.), wood free papers, art papers, coated papers, cast coated papers, wall papers, lining papers, papers impregnated with a synthetic resin or an emulsion, papers impregnated with a synthetic rubber latex, synthetic resin-sized papers, paper boards, cellulose fiber papers, polyolefin-coated papers (in particular, papers both the surfaces of which are coated with polyethylene), etc.; various plastic films or sheets of polyolefin, polyvinyl chloride, polyethylene terephthalate, polystyrene, polymethacrylate, polycarbonate, etc., applied with a treatment for imparting a white light reflecting property; and laminates of an optional combination of the foregoing materials.

For the heat transfer image-receiving material, a fluorescent whitening agent may be used. Examples thereof are described in K. Veenkataraman, *The Chemistry of Synthetic Dyes*, Vol. 5, Chapter 8, JP-A-61-143752, etc. Practical examples thereof are stilbene series compounds, coumarine series compounds, biphenyl series compounds, benzoxazolyl series compounds, naphthalimide series compounds, pyrazoline series compounds, carbostyryl series compounds, and 2,5-dibenzoxazolethiophene series compounds.

The fluorescent whitening agent can be used together with a fading inhibitor.

In this invention, it is preferable for improving the parting property between the heat transfer dye providing material and the heat transfer image-receiving material, to incorporate a parting agent in the layer constituting the dye providing material and/or the image-receiving material, in particular, in the outermost layer at which both the materials are brought into contact with each other.

As the parting agent, solid or waxy materials such as polyethylene wax, amide wax, Teflon powder, etc.; surface active agents such as fluorine series surface active agents, phosphoric acid ester series surface active agents, etc.; oils such as paraffin series oils, silicone series oils, fluorine series oils, etc., which are conventionally known as parting agents, can be used, but the use of a silicone oil is particularly preferable.

As a silicone oil, a non-modified silicone oil and modified silicone oils such as carboxy-modified oils, amino-modified oils, epoxy-modified oils, etc., can be used.

As the examples of these silicone oils, various modified silicone oils described in *Modified Silicone Oil*, pages 6 to 18B, published by Shin-Etsu Silicone Co., Ltd. can be used. In the case of using a silicone oil in an organic solvent-soluble binder, an amino-modified silicone oil having a group capable of reacting with a crosslinking agent of the builder (e.g., a group capable of reacting an isocyanate) is effective. And in the case of using a silicone oil by emulsion-dispersing a water-soluble binder, a carboxy-modified silicone oil (e.g., X-22-3710, trade name, made by Shin-Etsu Silicone Co., Ltd.) is effective.

For hardening a water-soluble polymer, the hardening agents described in U.S. Pat. No. 4,678,739, column 41, JP-A-59-116655, JP-A-62-245261, and JP-A-6118942 are suitable. Practical examples of the hardening agent include aldehyde series hardening agents (formaldehyde, etc.), aziridine series hardening agents, epoxy series hardening agents

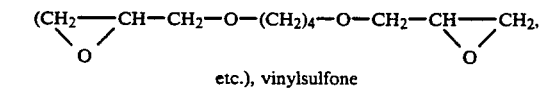

etc.), vinylsulfone sulfone series hardening agents [N,N'-ethylene-bis(-vinylsulfonylacetamido)ethane, etc.], N-methylol series hardening agents (dimethylolurea, etc.), and high molecular weight hardening agents (the compounds described in JP-A-62-234157).

For the heat transfer dye providing material and the heat transfer image-receiving material, a fading inhibitor may be used. The fading inhibitor include antioxidants, ultraviolet absorbents, and certain kinds of metal complexes.

The antioxidants include chroman series compounds, coumaran series compounds, phenol series compounds (e.g., hindered phenols), hydroquinone derivatives, hindered amine derivatives, spiroindane series compounds, etc. Also, the compounds described in JP-A-61-159644 are effective as the antioxidant.

The ultraviolet absorbents include benzotriazole series compounds (as described in U.S. Pat. No. 3,533,794, etc.), 4-thiazolidone series compounds (as described in U.S. Pat. No. 3,352,681, etc.), benzophenone series compounds (as described in JP-A-56-2784, etc.), and the compounds described in JP-A-54-48535, JP-A-62-136641, and JP-A-61-88256. Also, the ultraviolet absorptive polymers described in JP-A-62-260152 are effective.

The metal complexes include the compounds described in U.S. Pat. Nos. 4,241,155, 4,245,018, columns 3–36, and 4,254,195, columns 3–8, JP-A-62-174741, JP-A-61-88256, pages 27–29, and JP-A-1-75568.

Also, examples of the useful fading inhibitor are described in JP-A-62-215272, pages 125–137.

The fading inhibitor for inhibiting fading of the dye transferred onto the image-receiving material may previously exist in the image-receiving material or may be supplied to the image-receiving material from outside by a method of transferring the fading inhibitor from the dye providing material.

The foregoing antioxidants, ultraviolet absorbents, and metal complexes may be used in combination. For the layers constituting the heat transfer dye providing material and the heat transfer image-receiving material, various surface active agents can be used for the purposes of aiding coating, improving the parting property of the materials, improving the sliding property, static prevention, development acceleration, etc.

Examples of the surface active agent include nonionic surface active agents such as saponin (a steroid series), alkylene oxide derivatives (e.g., polyethylene glycol, polyethylene glycol alkyl ethers, polyethylene glycol alkylaryl ethers, polyethylene glycol esters, polyethylene glycol sorbitan esters, polyalkylene glycol alkylamines, polyalkylene glycol alkylamides, and polyethylene oxide addition products of silicone), glycidol derivatives (e.g., alkenylsuccinic acid polyglyceride and alkylphenol polyglyceride), fatty acid esters of polyhydric alcohols, alkyl esters of saccharides, etc.; anionic surface active agents containing an acid group (such as a carboxy group, a sulfo group, a phospho group, a sulfuric acid ester group, a phosphoric acid ester group, etc.), such as alkylcarboxylates, alkylsulfonates, alkylnaphthalenesulfonates, alkylsylfuric acid esters, alkylphosphoric acid esters, N-acyl-N-alkyltaurines, sulfosuccinic acid esters, sulfoalkylpolyethylene alkylphenyl ethers, polyoxyethylene alkylphosphoric acid esters, etc.; amphoteric surface active agents such as amino acids, aminoalkylsulfonic acids, aminoalkylsulfuric acid esters, aminoalkylphosphoric acid esters, alkylbetaines, amine oxides, etc.; and cationic surface active agents such as alkylamine salts, aliphatic or aromatic quaternary ammonium salts, heterocyclic quaternary ammonium salts such as pyridinium, imidazolium, etc., phosphonium or sulfonium salts containing an aliphatic group or a heterocyclic ring.

Practical examples of these surface active agents ar described in JP-A-62-173463 and JP-A-62-183457. Also, in the case of dispersing the material capable of receiving the heat migrating dye, the parting agent, the fading inhibitor, the ultraviolet absorbent, the fluorescent whitening agent, and the other hydrophobic compounds in a water-soluble binder, the use of a surface active agent as a dispersion aid is preferable. For that purpose, in addition to the foregoing surface active agents, the surface active agents described in JP-A-59-157636, pages 37-38 are particularly preferably used.

Furthermore, the layers constituting the heat transfer dye providing material and the heat transfer image-receiving material may further contain an organofluoro compound for the purposes of improving the sliding property, static prevention, improving the parting property, etc. Typical examples of the organofluoro compound include fluorine series surface active agents described in JP-B-57-9053, columns 8-17 (the term "JP-B" as used herein means an "examined published Japanese patent application"), JP-A-61-20944, and JP-A-62-135826 and hydrophobic fluorine compounds such as oily fluorine compounds (such as fluorine oils, etc.) or solid fluorine compound resins (such as tetrafluoroethylene resins, etc.

For the heat transfer dye providing material and the heat transfer image-receiving material, a matting agent can be used. The matting agent may be one of compounds described in JP-A-61-88256, page 29, such as silicon dioxide, polyolefin, and polymethacrylate, and the compounds described in JP-A-63-274944 and JP-A-63-274952, such as benzoguanamine resin beads, polycarbonate resin beads, AS resin beads, etc.

The following examples are intended to illustrate the present invention in more detail, but not to limit it in any way.

EXAMPLE 1

The absorption characteristics of Dye 1 for use in this invention and Comparison Dye A shown below in ethyl acetate are shown in FIG. 1 of the accompanying drawing.

Comparison Dye A:

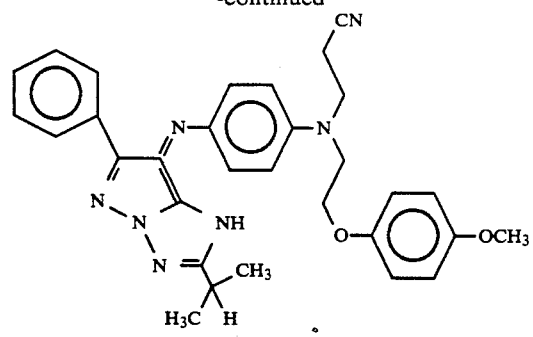

-continued

As is clear from FIG. 1, it can be seen that the absorption of Dye 1 for use in this invention is sharper than that of Comparison Dye A which has not substituent at the ortho position of the aryl group of the corresponding coupler moiety.

Also, in Dye 1 for use in this invention, the side absorption in the yellow region becomes less. (When the absorption of $\lambda_{max}$ is defined to be 1, the absorption at 425 nm is 0.073 for Comparison Dye A and 0.060 for Dye 1 in this invention.)

The $\lambda_{max}$ and the half value width of each of the dyes for use in this invention and those of Comparison Dye A and other comparison dyes shown below are shown in Table 1 below.

TABLE 1

| No. | Dye | | $\lambda_{max}$ (nm) | Half Value Width (nm) |
|---|---|---|---|---|
| 1 | 1 | Invention | 526 | 71 |
| 2 | A | Comparison | 524 | 75 |
| 3 | 5 | Invention | 529 | 71 |
| 4 | B | Comparison | 529 | 73 |
| 5 | 41 | Invention | 531 | 70 |
| 6 | C | Comparison | 531 | 73 |
| 7 | 42 | Invention | 529 | 70 |
| 8 | D | Comparison | 528 | 73 |
| 9 | 43 | Invention | 525 | 71 |
| 10 | E | Comparison | 524 | 74 |

(Values in ethyl acetate)

Comparison Dye B:

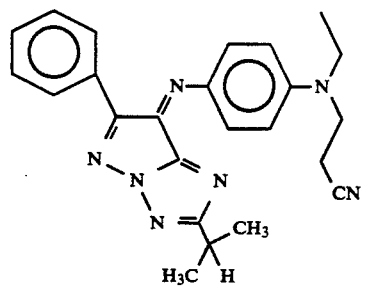

Comparison Dye C:

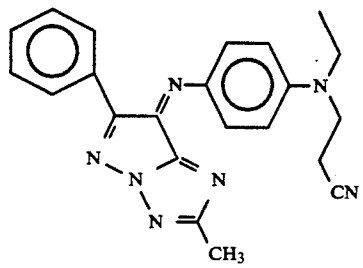

Comparison Dye D:

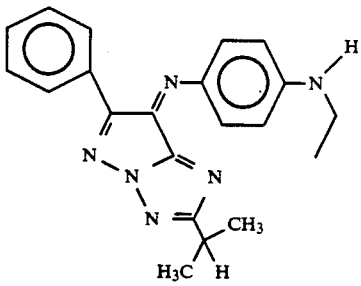

Comparison Dye E:

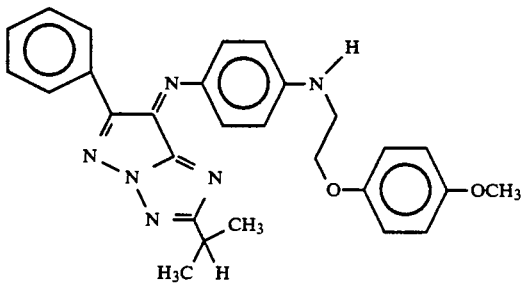

As is clear from the results shown in Table 1, it can be seen that in each case, the absorption of the dye for use in this invention is sharper than the absorption of the corresponding comparison dye having no substituent at the ortho-position.

EXAMPLE 2

Preparation of Heat Transfer Dye Providing Material (1-1)

As a support, a polyethylene terephthalate film of 6 μm in thickness (made by Teijin Limited), to the back surface of which was applied a heat resisting lubricating treatment, was used. On the surface of the film was coated a coating composition for a heat transfer dye providing layer having the composition shown below by wire bar coating at a dry thickness of 1.5 μm to provide heat transfer dye providing material (1-1).

| Coating Composition for Heat Transfer Dye Providing Layer | |
|---|---|
| Dye 1 | 3 g |
| Polyvinyl butyral resin (Denka Butyral 5000-A, trade name, made Denki Kagaku Kogyo K.K.) | 3 g |
| Toluene | 50 ml |
| Methyl Ethyl Ketone | 50 ml |
| Polyisocyanate (Takenate D110N, trade name, made by Takeda Chemical Industries, Ltd.) | 0.2 ml |

Then, by following the same procedure as in the case of preparing-heat transfer dye providing material (1-1), except that each of the dyes described in Table 2 below was used in place of Dye 1, heat transfer dye providing materials of this invention and comparison heat transfer dye providing materials (1-2) to (1-28) were prepared.

For determining the storage stability of each of the heat transfer dye providing materials, each sample was stored in a dry oven at 50° C. for one week and the heat stability thereof was tested.

Evaluation symbols are as follows:
○:Neither aggregation nor crystallization of the dye are obserbed by a microscope.
△:Aggregation and crystallization are slightly observed.
X:Overall aggregation and crystallization of the dye are visually observed.

The results obtained are shown in Table 2.

TABLE 2

| Heat Transfer Dye Providing Material | Dye | | Forcible Test Result |
|---|---|---|---|
| 1-1 | 1 | Invention | ○ |
| 1-2 | A | Comparison | △ |
| 1-3 | 5 | Invention | ○ |
| 1-4 | B | Comparison | △ |
| 1-5 | 41 | Invention | △ |
| 1-6 | C | Comparison | X |
| 1-7 | 42 | Invention | △ |
| 1-8 | D | Comparison | X |
| 1-9 | 43 | Invention | △ |
| 1-10 | E | Comparison | X |
| 1-11 | 2 | Invention | ○ |
| 1-12 | 3 | Invention | ○ |
| 1-13 | 4 | Invention | ○ |
| 1-14 | 13 | Invention | △ |
| 1-15 | 19 | Invention | ○ |
| 1-16 | 25 | Invention | ○ |
| 1-17 | 26 | Invention | △ |
| 1-18 | 27 | Invention | △ |
| 1-19 | 29 | Invention | ○ |
| 1-20 | 31 | Invention | ○ |
| 1-21 | 32 | Invention | ○ |
| 1-22 | 33 | Invention | ○ |
| 1-23 | 34 | Invention | ○ |
| 1-24 | 35 | Invention | ○ |
| 1-25 | 36 | Invention | ○ |
| 1-26 | 40 | Invention | ○ |
| 1-27 | F | Comparison | X |
| 1-28 | G | Comparison | X |

Comparison Dye F:

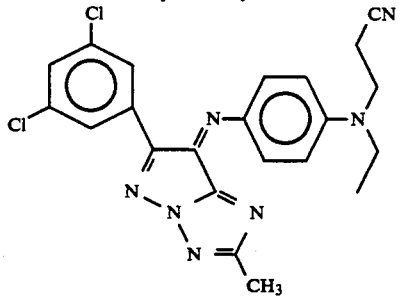

Comparison Dye G:

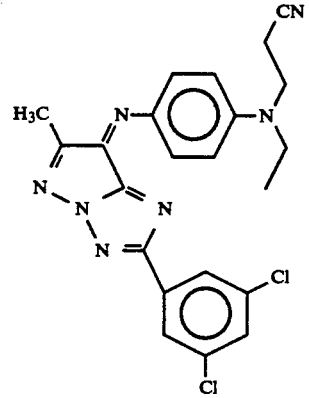

From the results shown in Table 2, it can be seen that the dyes for use in this invention are excellent in storage stability in the heat transfer providing materials.

EXAMPLE 3

Prepration of Heat Transfer Image-Receiving Material

As a base material, a synthetic paper of 150 μm in thickness (YUPO-FPG-150, trade name, made by Oji Yuka Goseishi Co., Ltd.) was used and a coating composition for an image-receiving layer having the composition shown below was coated on the surface of the paper by wire bar coating at a dry thickness of 8 μm to provide a heat transfer image-receiving material. Drying was carried out, after preliminary drying, in an oven set at 100° C. for 30 minutes.

| Coating Composition for Image-Receiving Layer | |
|---|---|
| Polyester Resin (Vylon-200, trade name, made by Toyobo Co., Ltd.) | 22 g |
| Polyisocyanate (KP-90, trade name, made by Dainippn Ink and Chemicals, Inc.) | 4 g |
| Amino-Midified Silicone Oil (KF-857, trade name, made by Shin-Etsu Silicone Co., Ltd.) | 0.5 g |
| Methyl Ethyl Ketone | 85 ml |
| Toluene | 85 ml |

Each of the heat transfer dye providing materials (1-1) to (1-14) and (1-21) obtained in Example 2 was superposed on the heat transfer image-receiving material obtained as described above so that the heat transfer dye providing layer was in contact with the image receiving layer. When printing was applied using a thermal head from the support side of the heat transfer dye providing material under the conditions of the output of the thermal head of 0.25 W/dot, the pulse width of from 0.1 msec. to 10 msec., and the dot density of 6 dots/mm to imagewise dye the image-receiving layer of the image-receiving material with the magenta color dye, a sharp image record having no transfer unevenness was obtained.

Then, the reflection density of each heat transfer image-receiving material thus recorded was measured.

Furthermore, each heat transfer image-receiving material thus recorded was exposed to a fluorescent lamp of 17,000 lux for 7 days to determine the stability of the color images. Before and after the light exposure, the status A reflection density thereof was measured and the stability was evaluated by the ratio.

The results are shown in Table 3.

TABLE 3

| No. | Heat Transfer Dye Providing Material | Dye | | Maximum Density | Light Fastness |
|---|---|---|---|---|---|
| 1 | 1-1 | 1 | Invention | 2.1 | 0.94 |
| 2 | 1-2 | A | Comparison | 2.1 | 0.93 |
| 3 | 1-3 | 5 | Invention | 2.5 | 0.82 |
| 4 | 1-4 | B | Comparison | 2.4 | 0.81 |
| 5 | 1-5 | 41 | Invention | 2.0 | 0.84 |
| 6 | 1-6 | C | Comparison | 2.0 | 0.83 |
| 7 | 1-7 | 42 | Invention | 1.7 | 0.85 |
| 8 | 1-8 | D | Comparison | 1.5 | 0.84 |
| 9 | 1-9 | 43 | Invention | 2.5 | 0.90 |
| 10 | 1-10 | E | Comparison | 2.5 | 0.90 |
| 11 | 1-11 | 2 | Invention | 2.1 | 0.95 |
| 12 | 1-12 | 3 | Invention | 2.2 | 0.90 |
| 13 | 1-13 | 4 | Invention | 2.2 | 0.91 |
| 14 | 1-14 | 13 | Invention | 2.0 | 0.94 |

TABLE 3-continued

| No. | Heat Transfer Dye Providing Material | Dye | | Maximum Density | Light Fastness |
|---|---|---|---|---|---|
| 15 | 1-21 | 32 | Invention | 2.1 | 0.94 |

From the results shown in Table 3, it can be seen that the dyes for use in this invention give a transfer density which is almost the same as or higher than the corresponding comparison dye having no substituent at the ortho-position. Also, the light-fastness of the dye for use in this invention is almost the same as or higher than the corresponding comparison dye having no substituent at the ortho-position.

EXAMPLE 4

By following the same procedure as in Example 2, except that each of the dyes shown in Table 4 below was used in place of Dye 1 in the coating composition for the heat transfer dye providing layer, heat transfer dye providing materials (2 - 1) to (2 - 11) were prepared.

Also, when printing was carried out using the image receiving material prepared in Example 3, a sharp image record having no transfer unevenness, a high density and an excellent light fastness was obtained in each case.

TABLE 4

| No. | Dye-Providing Material | Dye |
|---|---|---|
| 1 | 2-1 | 6 |
| 2 | 2-2 | 7 |
| 3 | 2-3 | 10 |
| 4 | 2-4 | 11 |
| 5 | 2-5 | 14 |
| 6 | 2-6 | 17 |
| 7 | 2-7 | 23 |
| 8 | 2-8 | 30 |
| 9 | 2-9 | 37 |
| 10 | 2-10 | 38 |
| 11 | 2-11 | 39 |

EXAMPLE 5

By following the same procedure as in Example 2, except that each of the resins and each of the dyes shown in Table 5 was used in place of the polyvinyl butyral resin and the dye in the coating composition for the heat transfer dye providing layer, heat transfer dye providing materials (3-1), (3-2), and (3-3) were prepared.

When printing was applied using the image-receiving material as in Example 3, sharp image records having no transfer unevenness as shown in Table 5 below were obtained. Also, the light fastness of the image records was excellent in each case.

TABLE 5

| Dye Providing Material | Resin | Dye | Maximum Density | Light Fastness |
|---|---|---|---|---|
| 3-1 | Ethyl cellulose | 1 | 2.1 | 0.92 |
| 3-2 | Cellulose acetate butyrate | 5 | 2.4 | 0.84 |
| 3-3 | Polysulfone | 13 | 2.0 | 0.94 |

Examples of a combination of other heat transfer image-receiving material and the foregoing heat transfer dye providing material of this invention are shown below.

EXAMPLE 6

Preparation of Heat Transfer Image-Receiving material

As a support, a synthetic paper of 150 μm in thickness (YUPO-FPG-150, trade name, made by Oji Yuka Goseishi Co., Ltd.) was used and a coating composition for an image-receiving layer having the following composition was coated on the surface of th synthetic paper by wire bar coating at a dry thickness of 10 μm to provide heat transfer image-providing material. Drying was carried out, after preliminary drying, in an oven set at 100° C. for 30 minutes.

| Composition for Image-Receiving Layer | |
|---|---|
| Polyester Resin No. 1 | 2.0 g |
| Amino-Modified Silicone Oil (KF 857, Shin-Etsu Silicone Co., Ltd.) | 0.5 g |
| Epoxy-Bodified Silicone Oil (KF 100T, Shin-Etsu Silicone Oil Co., Ltd.) | 0.5 g |
| Methyl Ethyl Ketone | 85 ml |
| Toluene | 85 ml |

Polyester Resin No. 1:

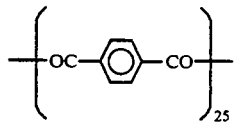

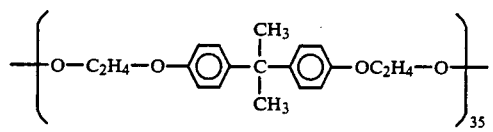

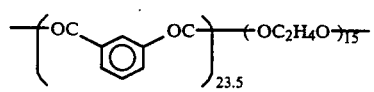

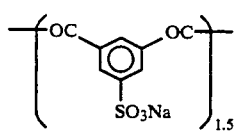

When printing was applied to a combination of the heat transfer image-receiving material with the heat transfer dye providing material in Example 3 or Example 4 as in Example 3, a sharp image record was obtained. Also, the image record was excellent in light fastness.

EXAMPLE 7

Preparation of Heat Transfer Image-Receiving Material

A resin coated paper obtained by coating polyethylene on both the surfaces of a paper of 200 μm in thickness, at thicknesses of 15 μm and 25 μm, respectively was prepared. A coating composition for an image-receiving layer having the following ocmposition was coated on the surface of the paper having a resin coating of 15 μm thickness by wire bar coating at a dry thickness of 10 μm followed by drying to provide a heat transfer image-receiving material.

| Coating Composition for Image-Receiving Layer | |
|---|---|
| Polyester Resin No. 1 | 25 g |
| Amino-Modified Silicone Oil (KF-857, trade name, made by Shin-Etsu Silicone Co., Ltd.) | 0.8 g |
| Polyisocyanate (KP-90, trade name, made by Dainippon Ink and Chemicals, Inc.) | 4 g |
| Methyl Ethyl Ketone | 100 ml |
| Toluene | 100 ml |

When printing was applied as in Example 6, a sharp image record having a high density was obtained. Also, the image record was excellent in light fastness.

EXAMPLE 8

Preparation of Heat Transfer Image-Receiving Material

In an aqueous gelatin solution having the following composition (A') was dispersed by emulsification an organic solvent solution of a dye receptive polymer having following composition (B') by a homogenizer to provide a gelatin dispersion of the dye receptive material.

| Aqueous Gelatin Solution (A') | |
|---|---|
| Gelatin | 2.3 g |
| Sodium Dodecylbenzenesulfonate (5% aqueous solution) | 20 ml |
| Water | 80 ml |
| Dye Receptive Polymer Solution (B') | |
| Polyester Resin (Vylon 300, trade name, made by Toyobo Co., Ltd.) | 7.0 g |
| Carboxy-Modified Silicone Oil (X-22-3710, trade name, made by Shin-Etsu Silicone Co., Ltd.) | 0.7 g |
| Methyl Ethyl Ketone | 20 ml |
| Toluene | 10 ml |
| Triphenyl Phosphate | 1.5 g |

By adding to the dispersion thus prepared a solution of 0.5 g of fluorine series surface active agent (a),

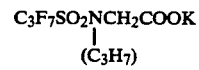

dissolved in 10 ml of a mixed solvent of water and methanol (1:1), a coating composition for an image-receiving layer was prepared. The coating composition was coated on a synthetic layer of 150 μm in thickness (YUPO-SGG-150, trade name, made by Oji Yuka Goseishi Co., Ltd.) to the surface of which was applied corona discharging at a wet thickness of 75 μm and dried to provide a heat transfer image-receiving material.

When recording of images was carried out as in Example 3 using each of the heat transfer dye providing materials obtained in Example 3 and Example 4 and the heat transfer image-receiving material obtained as described above, sharp images having a high density and a high light fastness were obtained in each case.

EXAMPLE 9

Preparation of Heat Transfer Image-Receiving Material

By following the same procedure as in Example 3 using the following coating composition for an image-receiving layer, a heat transfer image-receiving material was prepared.

Coating Composition for Image-Receiving layer

The same composition as the coating composition for image-receiving layer in Example 3 was used, except that 7 g of the ultraviolet absorbent shown below was added.

Ultraviolet Absorbent:

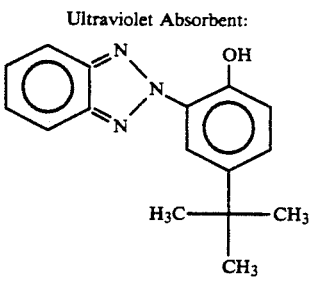

When printing was applied as in Example 3 using each of the heat transfer dye providing materials containing the dyes in this invention in Example 3 and Example 4, sharp images having a high density were obtained in each case. Also, the light fastness was higher than that obtained in the case of using the image-receiving material in Example 3.

EXAMPLE 10

By following the same procedure as in Example 2, except that each mixture of the dyes shown in Table 6 below was used in place of Dye 1 in the coating composition for the heat transfer dye providing layer, each of heat transfer dye providing materials (10-1) to (10-10) was prepared.

On each of the samples prepared, the heat stability test was carried out by the same manner as in Example 2.

Furthermore, printing was applied using the heat transfer image-receiving material in Example 3 by the same manner as in Example 3 and the reflection density of each sample was measured.

The results obtained are shown in Table 6.

TABLE 6

| Heat Transfer Dye Providing Material | Dye* | Heat Stability Test | Maximum Density |
| --- | --- | --- | --- |
| 10-1 | Dye 1 and Dye 13 | ◯ | 2.2 |
| 10-2 | Dye 1 and Dye 5 | ◯ | 2.5 |
| 10-3 | Dye 1 and Dye 32 | ◯ | 2.2 |
| 10-4 | Dye 1 and Dye 41 | ◯ | 2.2 |
| 10-5 | Dye 2 and Dye 5 | ◯ | 2.4 |
| 10-6 | Dye 2 and Dye 41 | ◯ | 2.2 |
| 10-7 | Dye 5 and Dye 41 | ◯ | 2.5 |
| 10-8 | Dye 41 and Dye 42 | ◯ | 2.0 |
| 10-9 | Dye 1 and Dye F | ◯ | 1.6 |
| 10-10 | Dye 1 and Dye G | ◯ | 1.5 |

*The amount of each dye was 1.5 g.

It can be seen from the above results that by using a mixture of two kinds of the dyes for use in this invention, the heat stability of the heat transfer dye providing material is improved.

Also, it can be seen that in the heat transfer dye providing materials (10-2), (10-5) and (10-7), the transfer maximum density is near the maximum density of the dye giving the highest density in the dyes used. Furthermore, it can be seen that in a combination of the mixed dyes each giving almost the same maximum density as in the case of the heat transfer dye providing materials (10-1), (10-3), (10-4), (10-6), and (10-8), a far higher density is obtained by using a mixture of the dyes.

Moreover, it can be seen that in the case of Comparison Dye F or G which can not give a stable heat transfer dye providing material singly, by using the dye as a mixture with the dye for use in this invention, the maximum denity of a substantially usable level is obtained and the heat transfer dye providing material becomes stable.

EXAMPLE 11

By following the same procedure as in Example 2, except that each mixture of the dyes shown in Table 7 shown below was used in place of Dye 1 in the coating composition for heat transfer dye providing layer, each of heat transfer dye providing materials (11-1) to (11-5) was prepared.

Printing was applied to each sample prepared using the heat transfer image-receiving material in Example 3 by the same manner as in Example 3.

Each sample obtained was stored for 2 weeks under severe conditions of 60° C. and 70% RH, and the bleeding property of the dyes was tested. The evaluation was visually made and a sample wherein the images became uneven and the density was lowered was evaluated as "Bleeding occured". The results are shown in Table 7.

TABLE 7

| Heat Transfer Dye Providing Material | Dye* | | Bleeding after Forcible Test | Remarks |
| --- | --- | --- | --- | --- |
| 11-1 | Dye 1 | 0.9 g | none | Invention |
| | Dye 48 | 2.1 g | | |
| 11-2 | Dye 1 | 1.5 g | none | Invention |
| | Dye 48 | 1.5 g | | |
| 11-3 | Dye 3 | 1.5 g | none | Invention |
| | Dye 48 | 1.5 g | | |
| 11-4 | Dye 5 | 1.5 g | none | Invention |
| | Dye 48 | 1.5 g | | |
| 11-5 | Dye G | 2.1 g | Occurred | Comparison |
| | Dye F | 0.9 g | | |

As is shown above, the images formed using the dyes for use in this invention do not cause bleeding in the image-receiving layer under the severe conditions, while images formed using the comparison dyes cause bleeding under the severe conditions.

As described above, it can be understood that the heat transfer dye providing material of this invention has a good storage stability and gives images having a high density at transfer.

Furthermore, the absorption of the dye for use in this invention is sharp and gives images having a high light fastness.

While the invention has been described in detail and with reference to specific embodiments thereof, it will be apparent to one skilled in the art that various changes and modifications can be made therein without departing from the spirit and scope thereof.

What is claimed is:

1. A heat transfer dye providing material having on a support a dye providing layer containing a heat migrating dye represented by following formula (I):

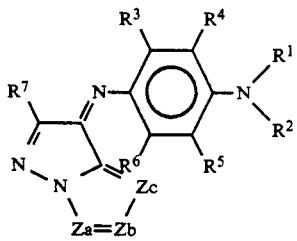 (I)

where $R^1$ and $R^2$ each independently represents a hydrogen atom, an alkyl group, an aryl group, or a heterocyclic group; $R^3$, $R^4$, $R^5$, $R^6$, and $R^7$ each independently represents a hydrogen atom or a non-metallic substituent; and Za, Zb, and Zc each independently represents —N= or

wherein $R^8$ represents a hydrogen atom or a non-metallic substituent, at least one of said $R^7$ and $R^8$ is an aryl group or a heterocyclic group each having a substituent at an ortho-position to the position bonded to the nitrogen-containing ring of formula (I); and said $R^3$ and $R^4$, said $R^4$ and $R^1$, said $R^1$ and $R^2$, said $R^2$ and $R^5$, and/or said $R^5$ and $R^6$ may combine with each other to form a ring structure; and when Za and Zb in formula (I) represent carbon atoms substituted by $R^8$ groups, those $R^8$ groups may combine with each other to form a ring structure.

2. The heat transfer dye providing material of claim 1, wherein $R^1$ and $R^2$ each represents an alkyl group having 1 to 6 carbon atoms.

3. The heat transfer dye providing material of claim 1, wherein $R^3$, $R^4$, $R^5$ and $R^6$ each separately represents a hydrogen atom, an alkyl group, an alkoxy group, an alkoxycarbonylamino group, an aminocarbonylamino group, an acylamino group or a sulfonylamino group.

4. The heat transfer dye providing material of claim 1, wherein $R^3$ represents a hydrogen atom, an alkyl group, an alkoxycarbonylamino group, an aminocarbonylamino group or an acylamino group, and $R^4$, $R^5$ and $R^6$ each represents a hydrogen atom.

5. The heat transfer dye providing material of claim 1, wherein the compound according to formula (I) is represented by one of the following formulae (II), (III), (IV), (V), (VI) or (VII):

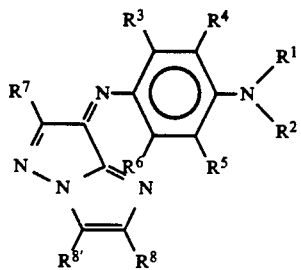 (II)

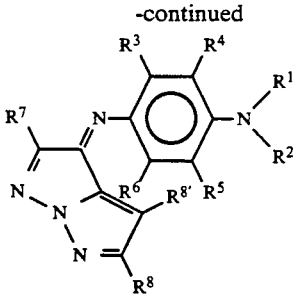 (III)

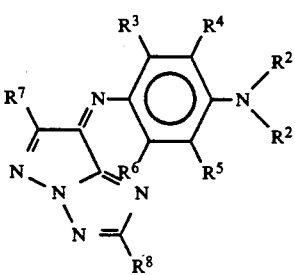 (IV)

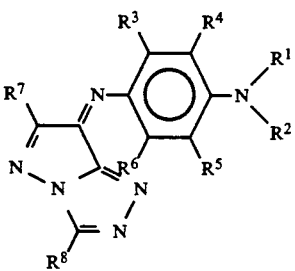 (V)

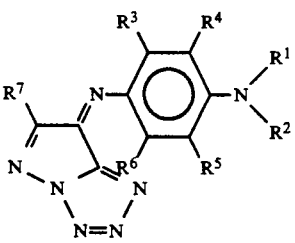 (VI)

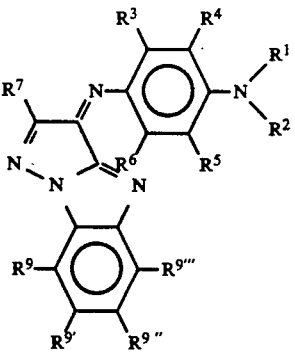 (VII)

wherein $R^8$ and $R^{8'}$ each represents a hydrogen atom or a non-metallic substituent, and $R^9$, $R^{9'}$, $R^{9''}$ and $R^{9'''}$ each represents the same groups as represented by $R^3$, $R^4$, $R^5$ and $R^6$, and $R^1$, $R^2$, $R^3$, $R^4$, $R^5$, $R^6$ and $R^7$ are as defined above.

6. The heat transfer dye providing material of claim 5, wherein the compound according to formula (I) is represented by formula (IV).

7. The heat transfer dye providing material of claim 5, wherein the compound according to formula (I) is represented by formula (V).

8. The heat transfer dye providing material of claim 5, wherein $R^8$ represents a hydrogen atom, an alkyl group, an aryl group, a heterocyclic group, an alkoxy group, an amino group, an alkoxycarbonyl group or an acyl group.

9. The heat transfer dye providing material of claim 8, wherein $R^8$ represents a substituted or unsubstituted alkyl group having 1 to 12 carbon atoms, a substituted or unsubstituted aryl group having 6 to 12 carbon atoms, or a substituted or unsubstituted heterocyclic group having 2 to 10 carbon atoms.

10. The heat transfer dye providing material of claim 1, wherein the aryl group or heterocyclic represented by at least $R^7$ or $R^8$ is represented by the following formula (VIII):

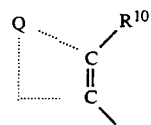

wherein Q represents an atomic group necessary for forming an aryl group or a heterocyclic group, and $R^{10}$ represents a hydrogen atom, or a non-metallic substituent.

11. The heat transfer dye providing material of claim 10, wherein $R^{10}$ represents a chlorine atom, a bromine atom, an alkyl group, an alkoxy group, an aryloxy group.

12. The heat transfer dye providing material of claim 10, wherein $R^{10}$ represents a chlorine atom or an alkoxy group.

13. The heat transfer dye providing material of claim 1, wherein the compound according to formula (I) is substituted by a group which has the effect of restraining fading.

* * * * *